United States Patent [19]

Boden et al.

[11] Patent Number: 4,983,579

[45] Date of Patent: Jan. 8, 1991

[54] CYANO-SUBSTITUTED SULFUR CONTAINING COMPOUNDS, COMPOSITIONS CONTAINING SAME, PROCESSES FOR PREPARING SAME AND ORGANOLEPTIC USES THEREOF

[75] Inventors: Richard M. Boden, Ocean; Joseph A. McGhie, Orange, both of N.J.

[73] Assignee: International Flavors & Fragrances Inc., New York, N.Y.

[21] Appl. No.: 545,841

[22] Filed: Jun. 29, 1990

Related U.S. Application Data

[60] Division of Ser. No. 424,601, Oct. 20, 1989, which is a continuation-in-part of Ser. No. 273,016, Nov. 18, 1988, Pat. No. 4,883,884.

[51] Int. Cl.$^5$ ............... C07C 255/17; C07C 327/02; A61K 7/46
[52] U.S. Cl. ........................ 512/6; 426/535; 558/251; 558/256
[58] Field of Search ............. 512/6; 558/251, 256; 426/535

[56] References Cited

U.S. PATENT DOCUMENTS

| | | | |
|---|---|---|---|
| 2,630,448 | 3/1953 | Crouch et al. | 558/256 |
| 3,140,295 | 7/1964 | Krespan | 558/251 X |
| 3,325,369 | 6/1967 | Somerville et al. | 512/6 X |
| 3,531,510 | 9/1970 | Blumenthal | 512/6 X |
| 4,277,377 | 7/1981 | Webb et al. | 512/6 |
| 4,625,046 | 11/1986 | Gebauer | 512/6 X |
| 4,883,884 | 11/1989 | Boden et al. | 549/74 |

Primary Examiner—Joseph Paul Brust
Attorney, Agent, or Firm—Arthur L. Liberman

[57] ABSTRACT

Described are cyano-substituted sulfur-containing compounds having the structures:

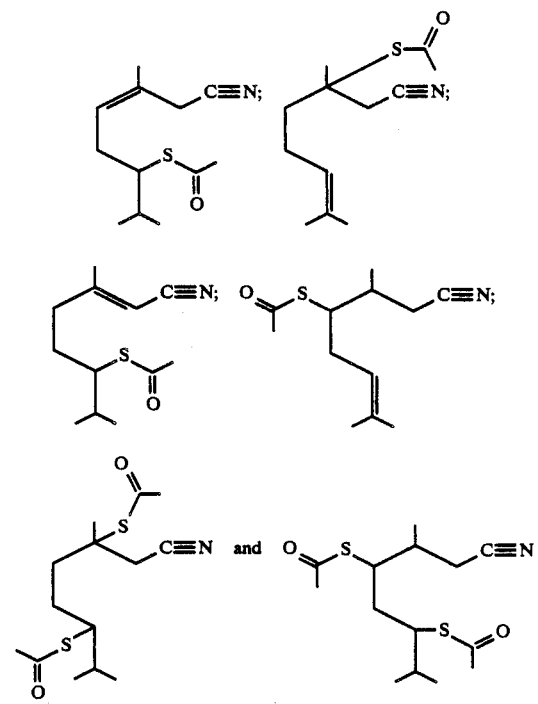

as well as organoleptic uses thereof.

4 Claims, 11 Drawing Sheets

GLC PROFILE FOR EXAMPLE I.
CRUDE

GLC PROFILE FOR EXAMPLE I. DISTILLATION FRACTION 6.

FIG. 3 NMR SPECTRUM FOR EXAMPLE I.

IR SPECTRUM FOR EXAMPLE I.

GLC PROFILE FOR EXAMPLE I(B). CRUDE

GLC PROFILE FOR EXAMPLE II.
CRUDE

GLC PROFILE FOR FRACTION 4 OF
EXAMPLE II. DISTILLATION.

FIG.9 NMR SPECTRUM FOR EXAMPLE II.

CYANO-SUBSTITUTED SULFUR CONTAINING COMPOUNDS, COMPOSITIONS CONTAINING SAME, PROCESSES FOR PREPARING SAME AND ORGANOLEPTIC USES THEREOF

This application is a divisional of application for U.S. Letters Patent, Ser. No. 424,601 filed on Oct. 20, 1989 which, in turn, is a continuation-in-part of application for U.S. Letters Patent, Ser. No. 273,016 filed on Nov. 18, 1988, now U.S. Pat. No. 4,883,884 issued on Nov. 28, 1989.

BACKGROUND OF THE INVENTION

This invention relates to hydroxyl-and-cyano-substituted sulfur-containing compounds having the structures:

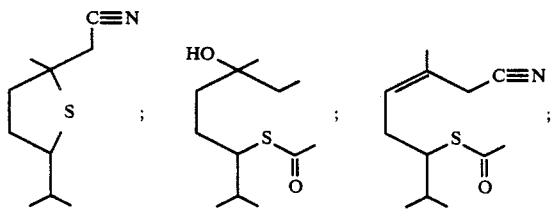

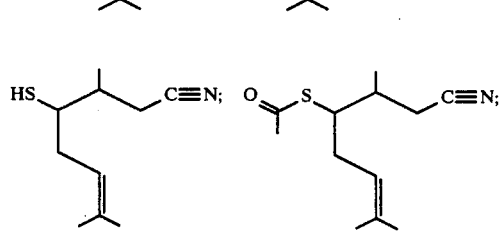

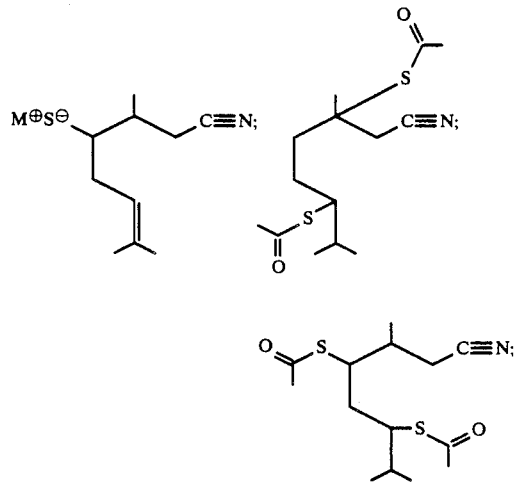

(wherein M is alkali metal) and compositions containing same produced by reaction of thioacetic acid with either (i) geranonitrile in the form of either the mixture of compounds having the structures:

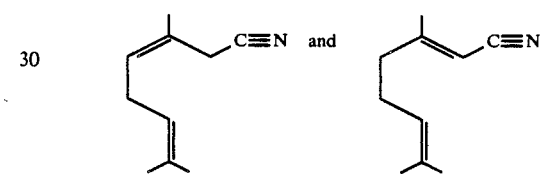

or the single compound having the structures:

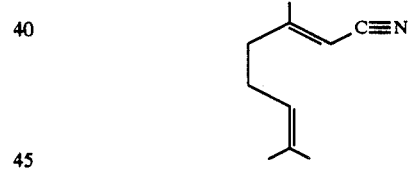

or (ii) dihydro linalool having the structure:

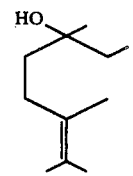

and uses of a subgenus thereof having the structures:

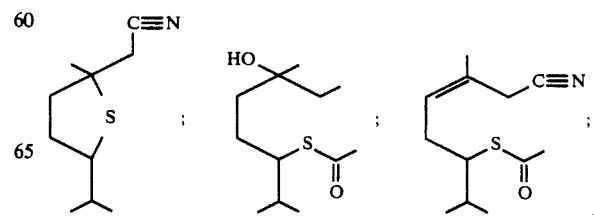

-continued

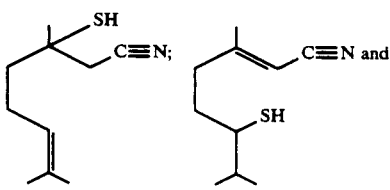

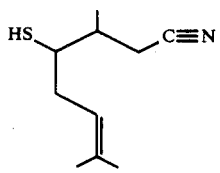

as well as products produced according to the foregoing processes in augmenting or enhancing the aroma or taste of consumable materials including perfume compositions, colognes, perfumed articles, foodstuffs and chewing gums.

There has been considerable work performed relating to substances which can be used to impart (or alter, modify or enhance) fragrances and aromas and/or tastes to (or in) perfume compositions, colognes, perfumed articles, foodstuffs and chewing gums. These substances are used to diminish the use of natural materials, some of which may be in short supply and/or to provide more uniform properties in the finished product.

Powerful, long-lasting, green, floral, rose, natural buchu leaf, tomato leaf, herbaceous, basil, minty and grapefruit-like aromas with natural "ontiga", tomato leaf, minty and grapefruit-like undertones are highly desirable to many types of perfume compositions, perfumes and perfumed articles, particularly herbal fragrances and herbal fragranced soaps and detergents.

Grapefruit and nootkatone-like aroma and taste nuances are highly desirable in the creation of flavors for foodstuffs and chewing gums.

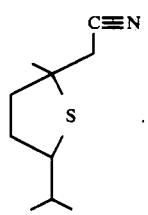

Figure 2:
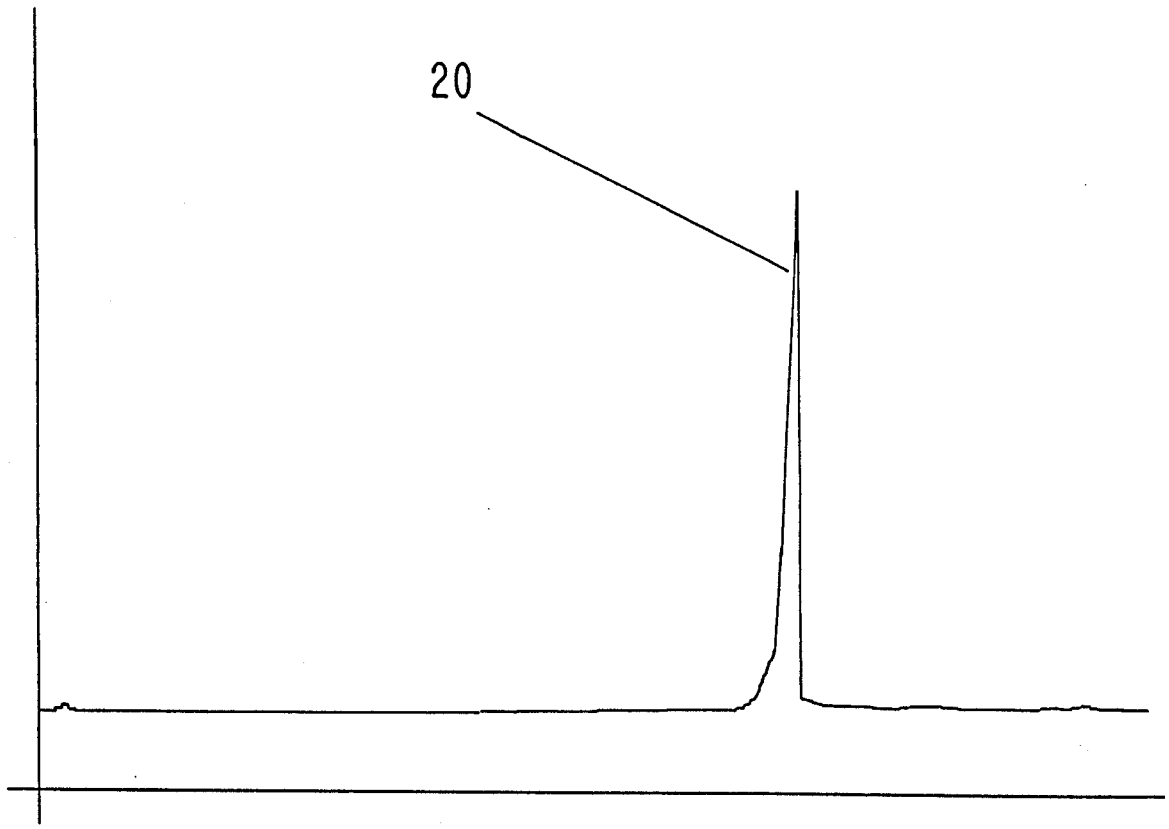

FIG. 2 is the GLC profile for fraction 6 of the distillation of the reaction produce of Example I(A) containing the compound having the structure:

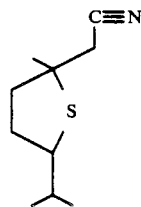

(Conditions: SE-30 column programmed at 100°-220° C. at 8° C. per minute).

Figure 3:
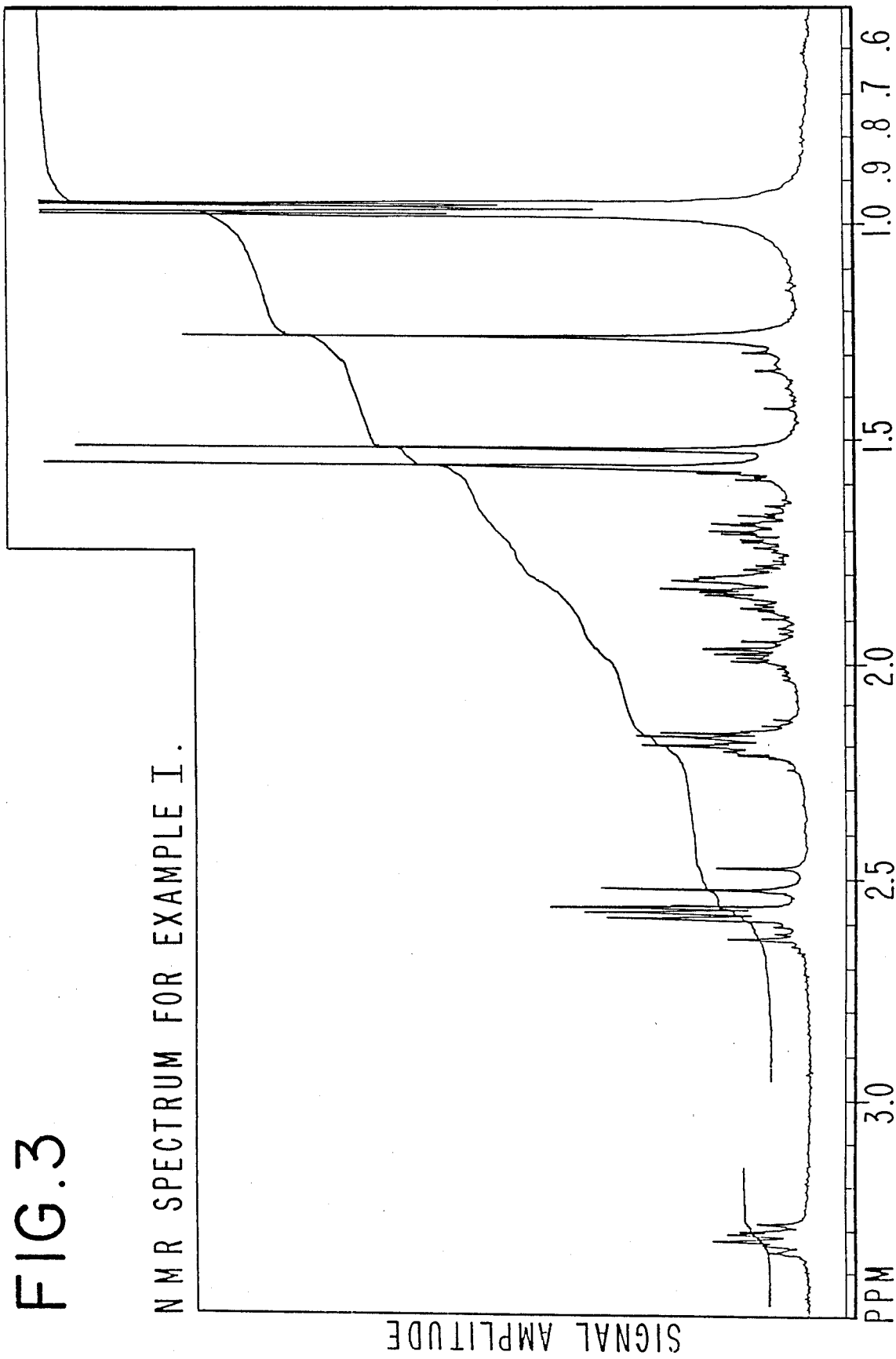

FIG. 3 is the NMR spectrum for the compound having the structure:

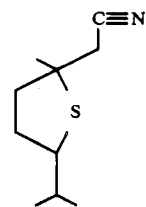

prepared according to Example I(A).

Figure 4:
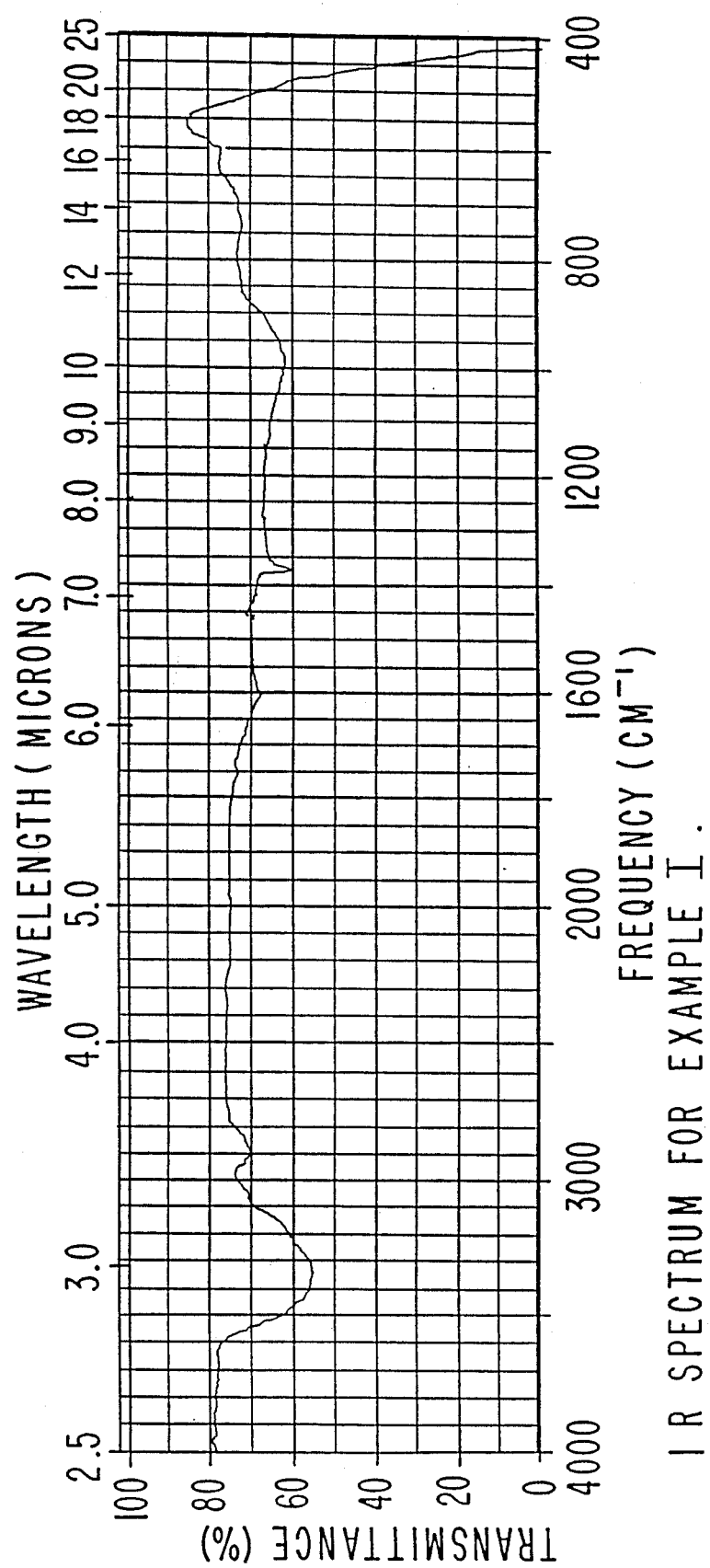

FIG. 4 is the infra-red spectrum for the compound having the structure:

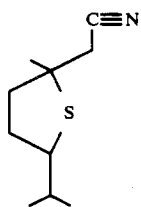

prepared according to Example I(A).

Figure 5:
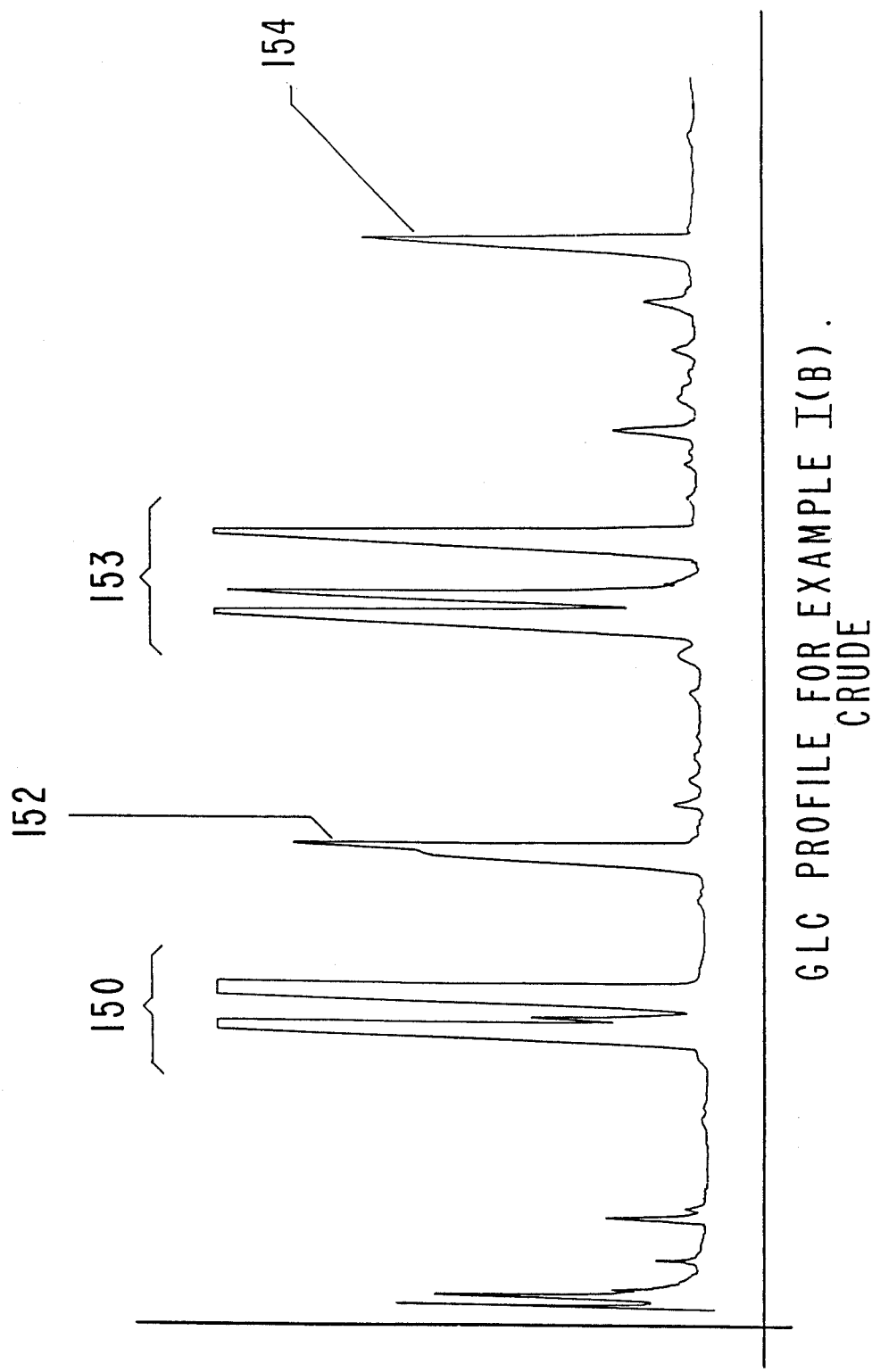

FIG. 5 is the GLC profile of the base-washed (NaHCO$_3$) crude reaction product of Example I(B) containing compounds having the structures:

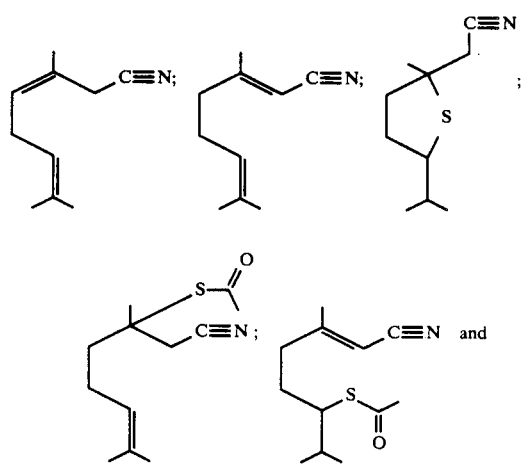

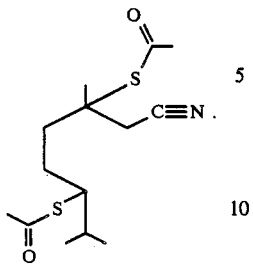

Figure 6:
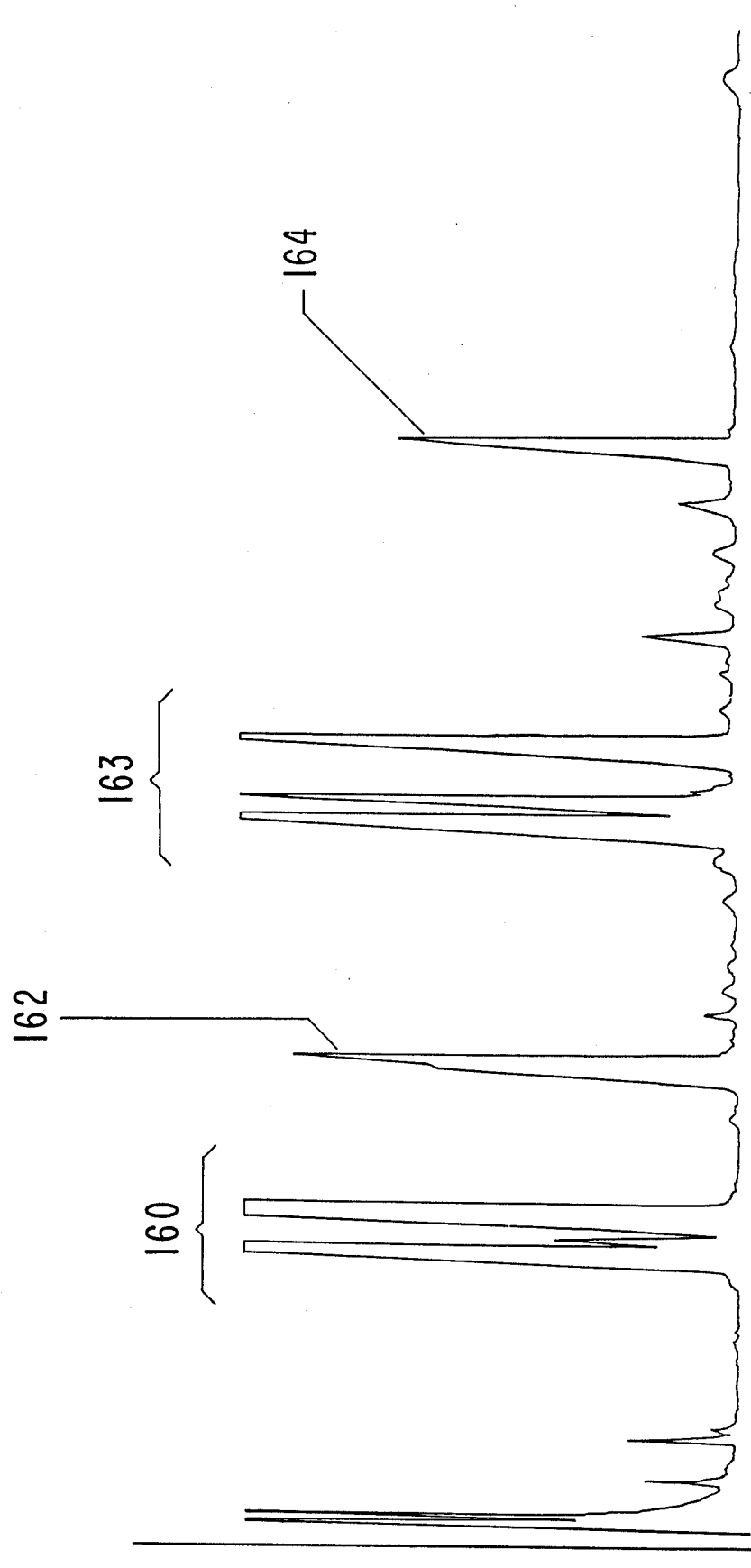

FIG. 6 is the GLC profile of the water-washed crude reaction product of Example I(B) containing compounds having the structures:

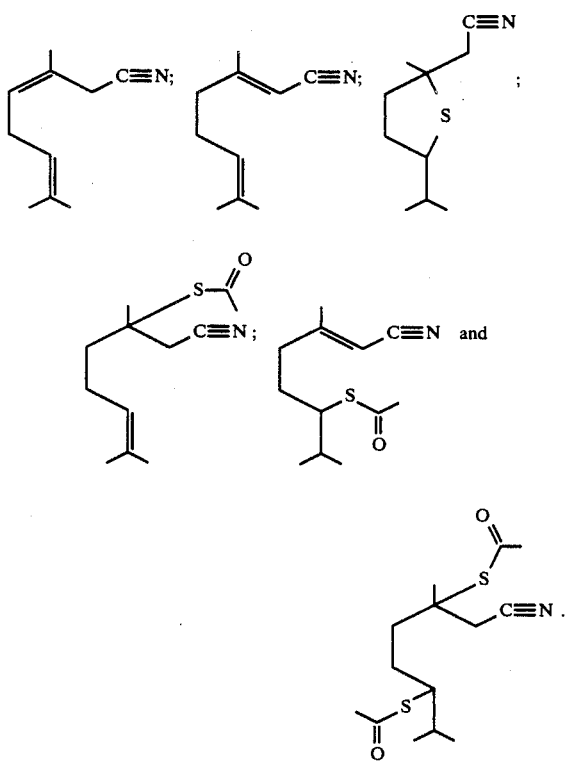

Figure 7:
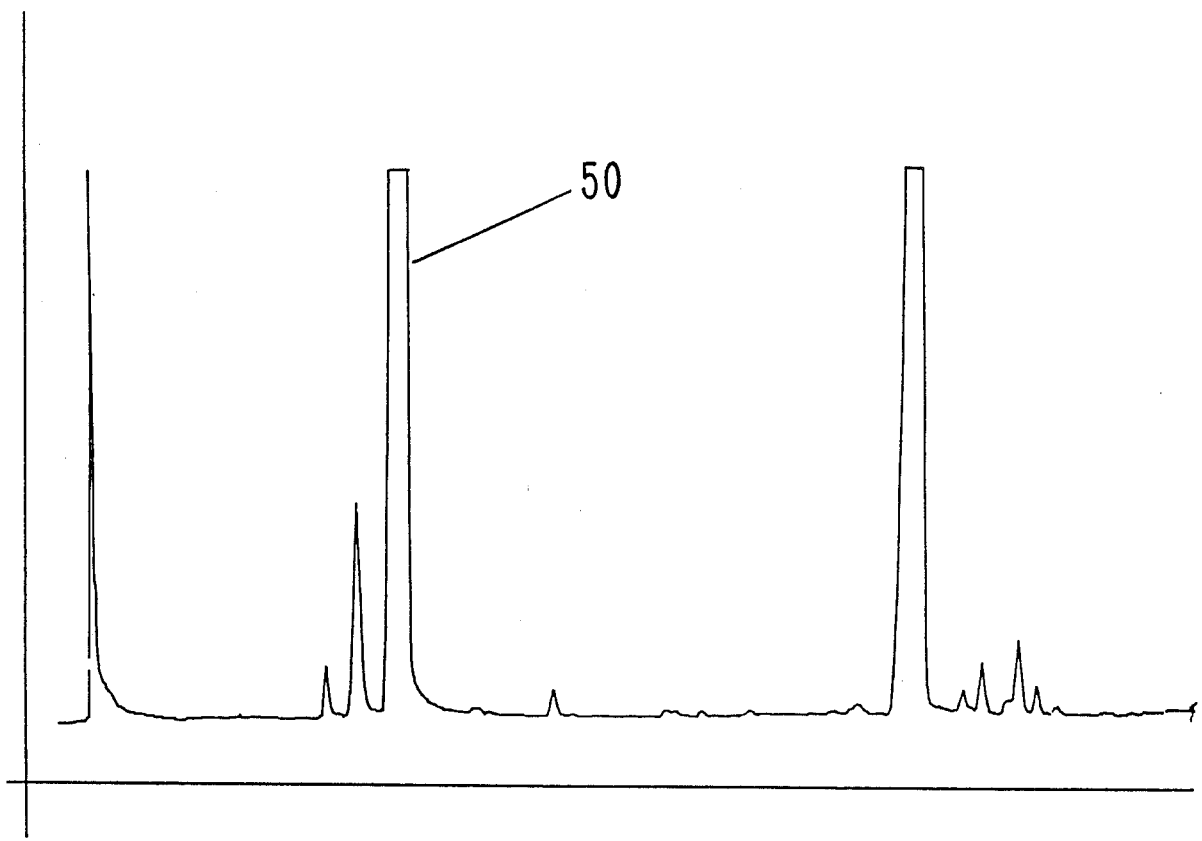

FIG. 7 is the GLC profile for the crude reaction product of Example II containing the compound having the structure:

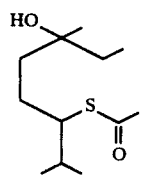

(Conditions SE-30 column programmed at 100°-220° C. at 8° C. per minute)

Figure 8:
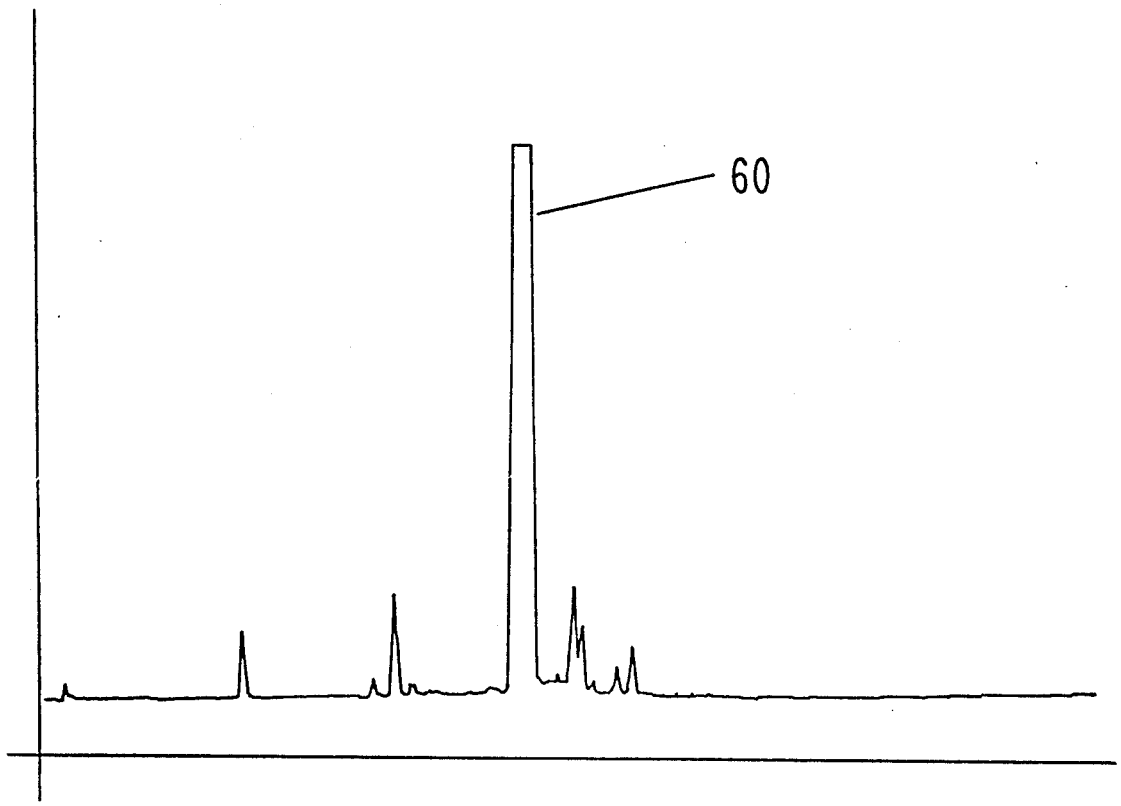

FIG. 8 is the GLC profile for fraction 4 of the distillation of the reaction product of Example II containing the compound having the structure:

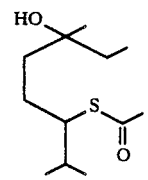

(Conditions: SE-30 column programmed at 100°-220° C. at 16° C. per minute).

Figure 9:
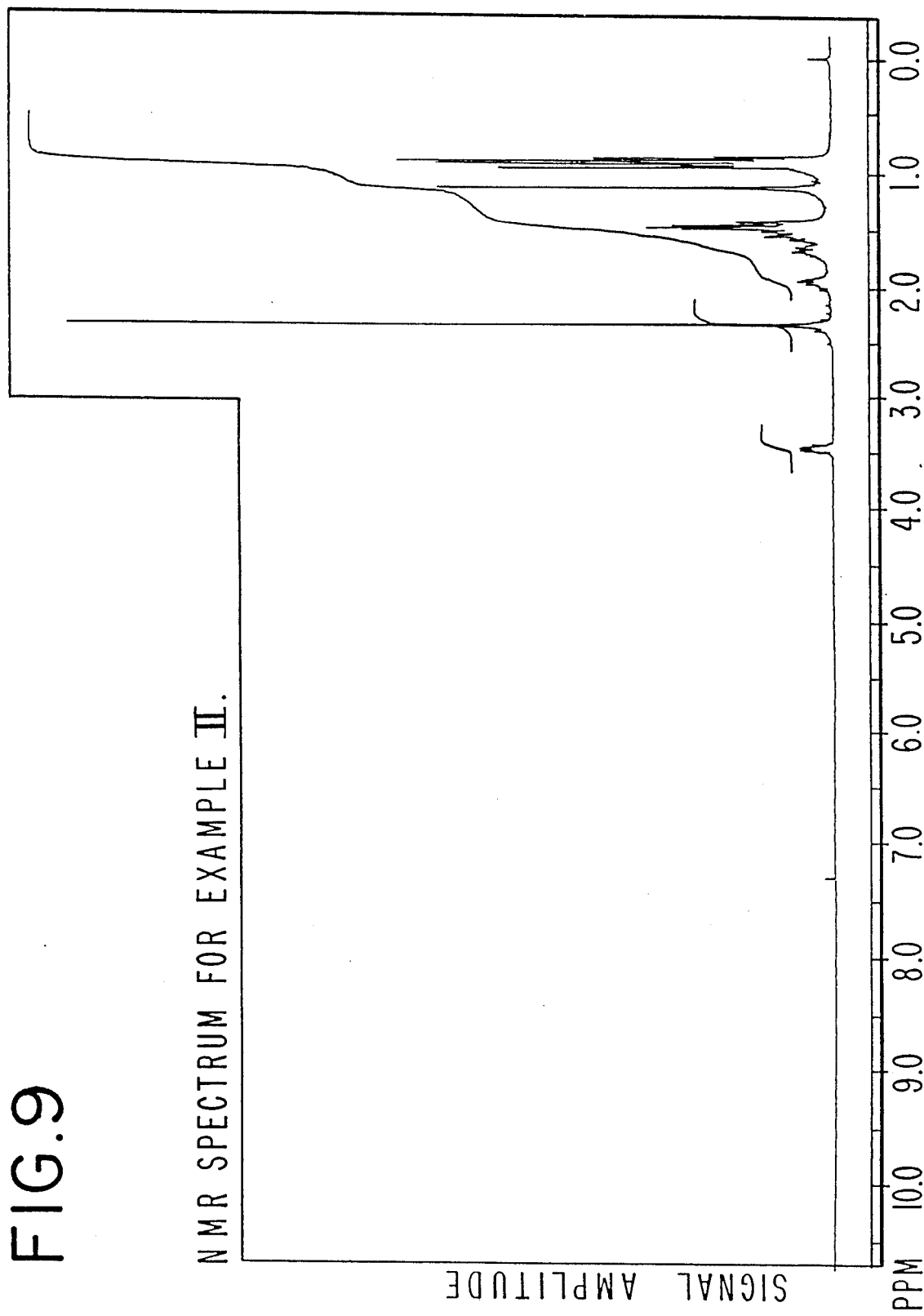

FIG. 9 is the NMR spectrum for the compound having the structure:

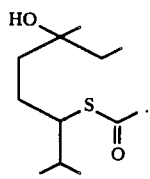

Figure 10:
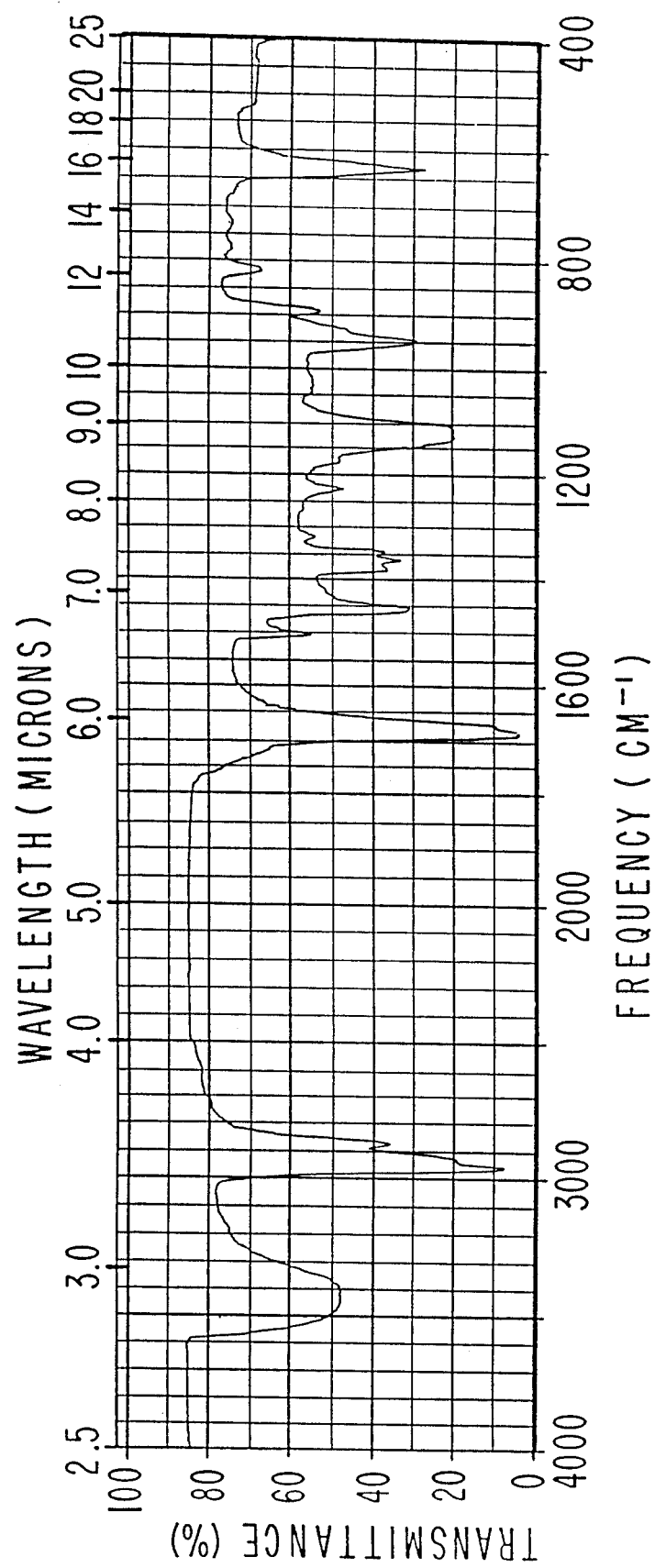

FIG. 10 is the infra-red spectrum for the compound having the structure:

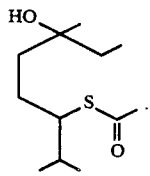

Figure 11:
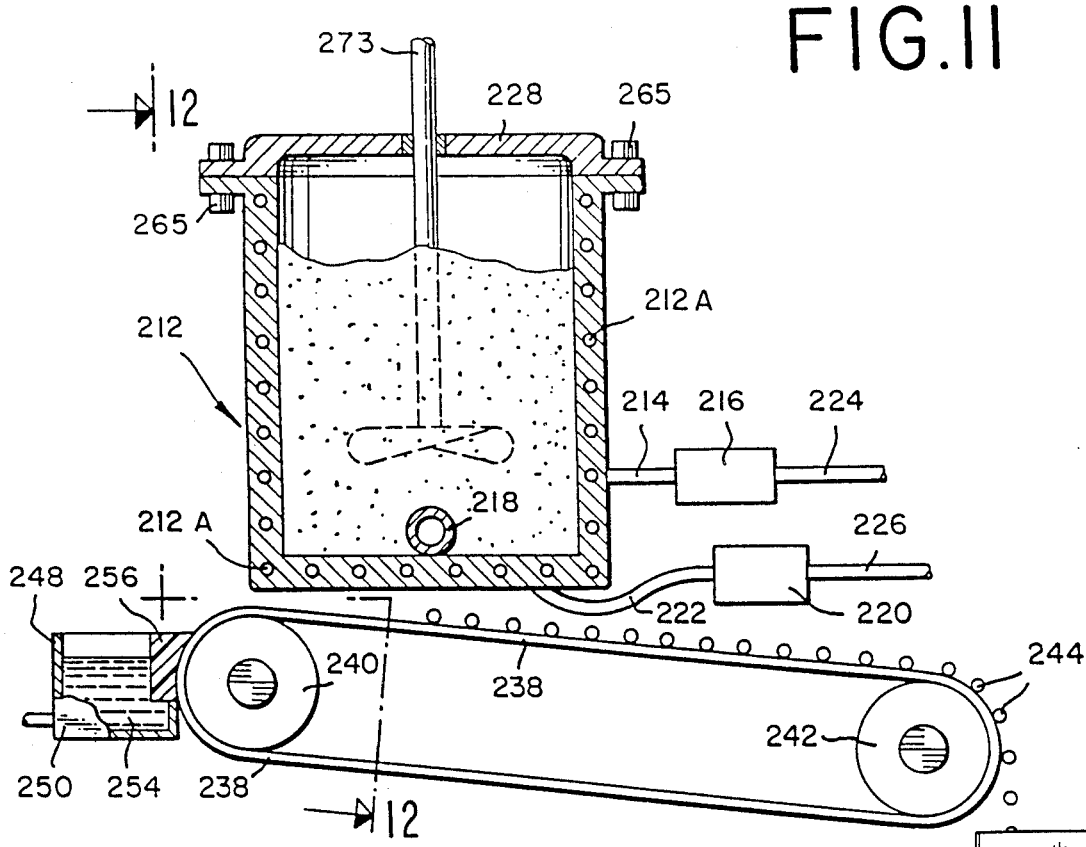

FIG. 11 is a cut-away side elevation view of apparatus used in preparing the fragrance containing polymers of our invention.

Figure 12:
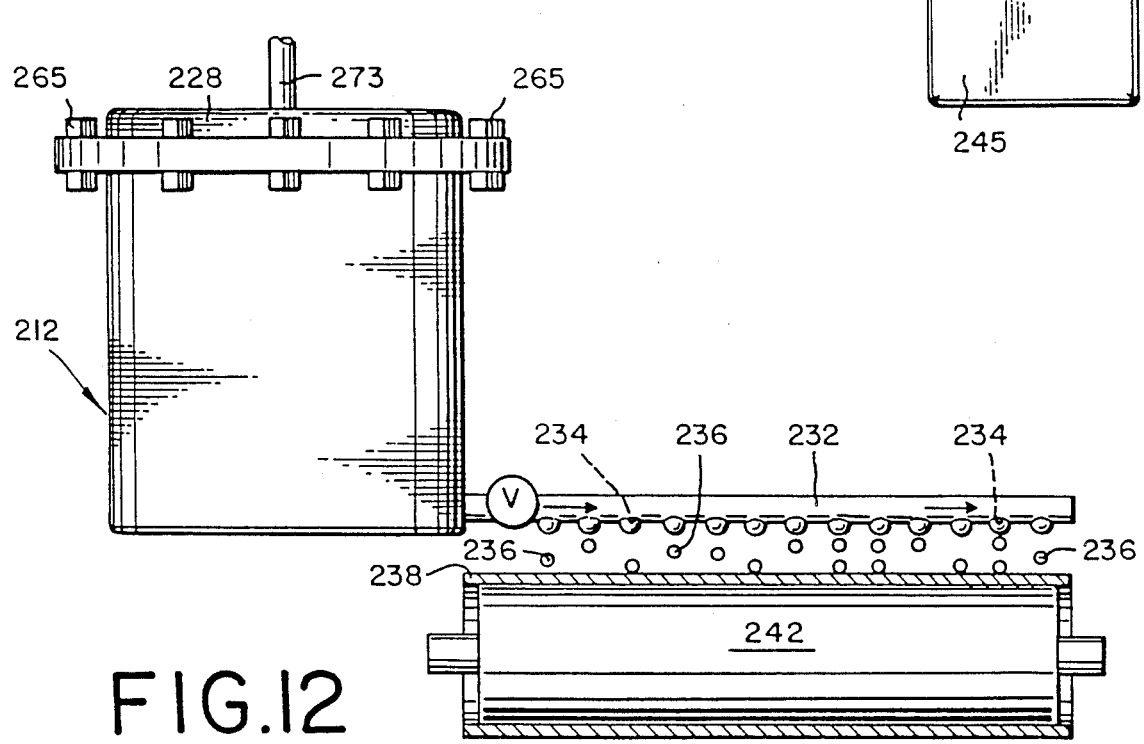

FIG. 12 is a cross sectional view taken along lines 12—12 of FIG. 11.

DETAILED DESCRIPTION OF THE DRAWINGS

Figure 1:
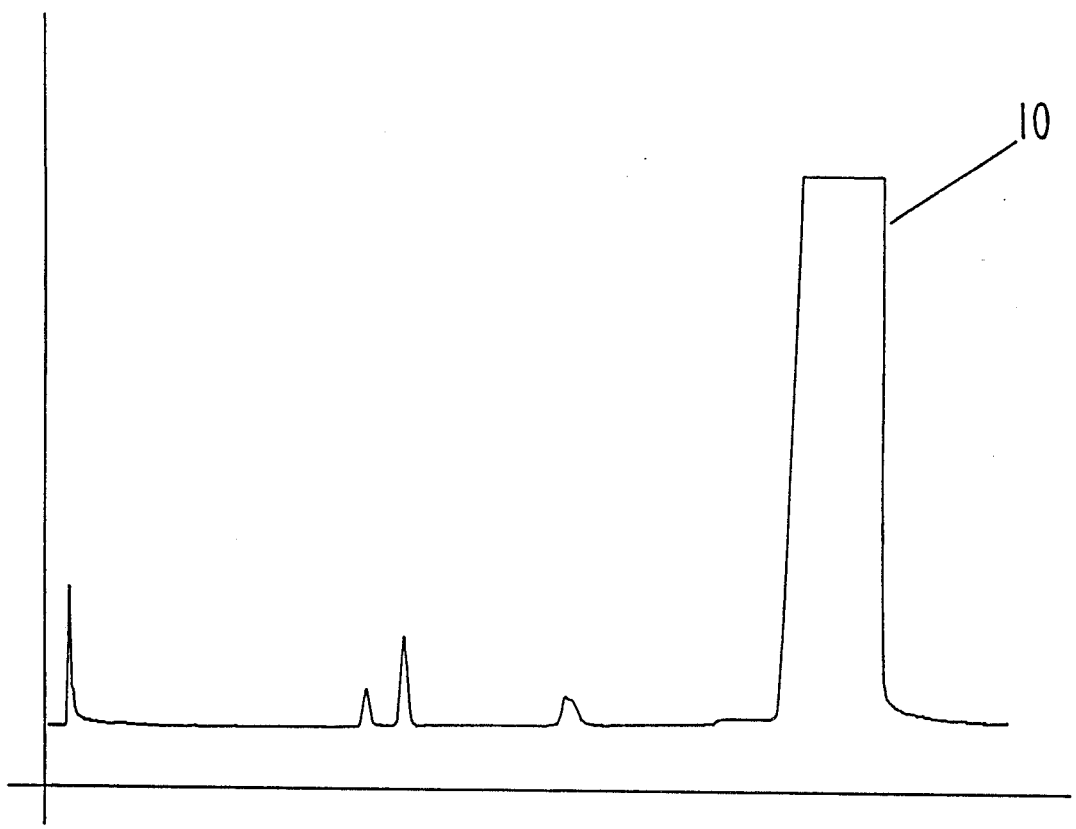
FIG. 1 is the GLC profile for the crude reaction product of Example I(A) containing the compound having the structure.

FIG. 1 is the GLC profile for the crude reaction product of Example I(A) containing the compound having the structure:

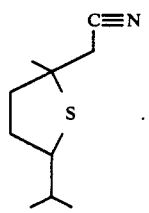

The peak indicated by reference numeral 10 is the peak for the compound having the structure:

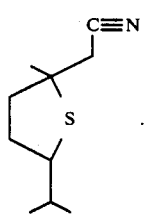

FIG. 2 is the GLC profile for fraction 6 of the distillation of the reaction product of Example I(A). (Conditions: SE-30 column programmed at 100°–220° C. at 8° C. per minute). The peak indicated by reference numeral 20 is the peak for the compound having the structure:

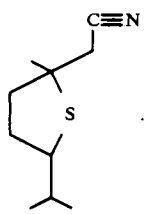

FIG. 5 is the GLC profile for the base-washed crude reaction product of Example I(B)(washed with sodium bicarbonate). The peaks indicated by reference numeral 150 are the peaks for the compounds having the structures:

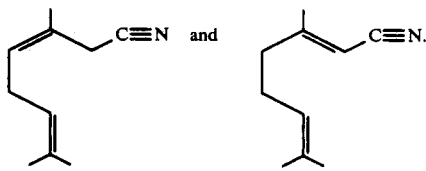

The peak indicated by reference numeral 152 is the peak for the compound having the structure:

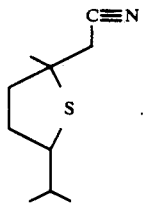

The peaks indicated by reference numeral 153 are the peaks for the compounds having the structures:

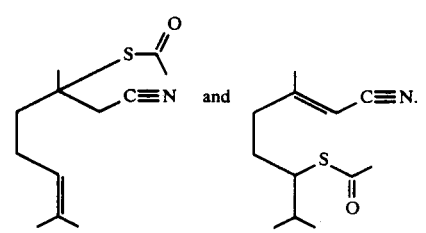

The peak indicated by reference numeral 154 is the peak for the compound having the structure:

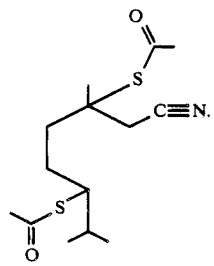

FIG. 6 is the GLC profile for the crude water-washed reaction product of Example I(B). The peaks indicated by reference numeral 160 are the peaks for the compounds having the structures:

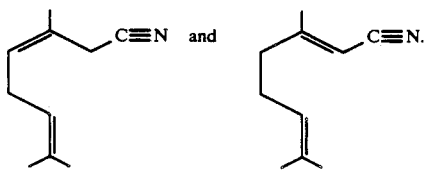

The peak indicated by reference numeral 162 is the peak for the compound having the structure;

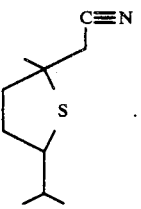

The peaks indicated by reference numeral 163 are the peaks for the compounds having the structures:

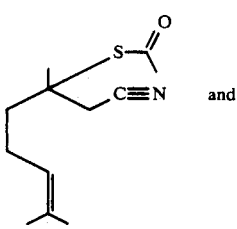

The peak indicated by reference numeral 164 is the peak for the compound having the structure:

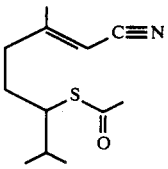

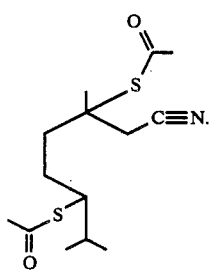

FIG. 7 is the GLC profile for the crude reaction product of Example II. The peak indicated by reference numeral 50 is the peak for the compound having the structure:

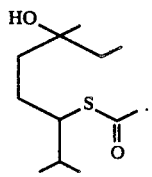

FIG. 8 is the GLC profile for fraction 4 of the distillation of the reaction product of Example II. The peak indicated by reference numeral 60 is the peak for the compound having the structure:

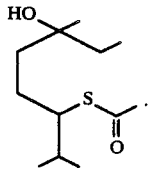

Referring to FIGS. 11 and 12, a thermoplastic polymer, e.g., polyethylene is heated to about 220°–250° C. in a container 212 of the kind illustrated in FIGS. 11 and 12. A formulation containing of at least one of the organoleptically useful hydroxyl-and-cyano-substituted sulfur-containing compounds of our invention having one of the structures:

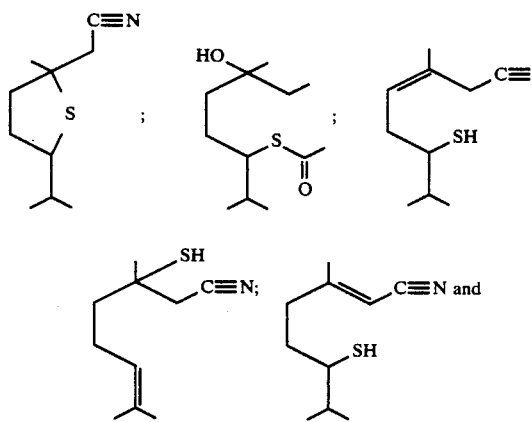

-continued

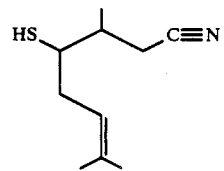

is then quickly added to the liquified thermoplastic polymer. The lid 228 is put in place and the agitating means 273 is actuated. The temperature is maintained at about 225° F. and the mixing is continued for about 5–15 minutes. The valve "V" is then opened to allow flow of the molten thermoplastic polymer enriched with the fragrance containing at least one of the organoleptically useful hydroxyl-and-cyano-substituted sulfur-containing compounds of our invention to exit through the orifices 234. The liquid falling through the orifices 234 solidifies almost instantaneously upon impact with the moving cooled conveyor 238. The thermoplastic polymer beads or pellets 224 having pronounced aromas which are aesthetically pleasing are thus formed.

The conveyor 238 is moved using conveyor rollers 240 and 242. The vessel 212 is heated using heating coils 212A using power input supplies indicated by reference numerals 214, 216, 224, 222, 220 and 226. The solidified beads containing fragrance containing the at least one of the organoleptically useful hydroxyl-and-cyano-substituted sulfur-containing compounds of our invention are indicated by 244 traveling into container 245 where they are used for subsequent processing. The conveyor is cooled using a cooling device indicated by reference numerals 248, 256, 215 and 254.

THE INVENTION

The invention relates to hydroxyl-and-cyano-substituted sulfur-containing compounds defined according to the structures:

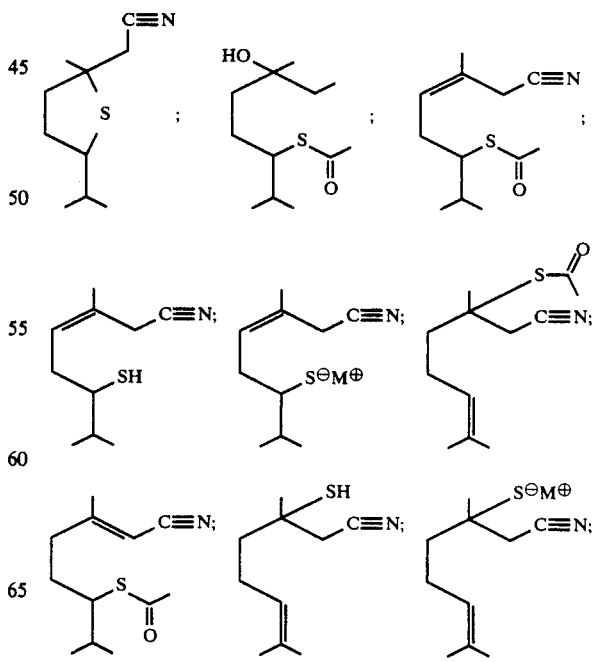

-continued

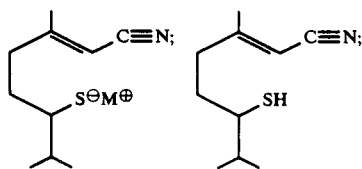

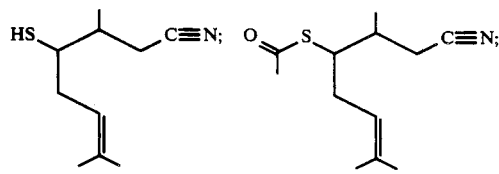

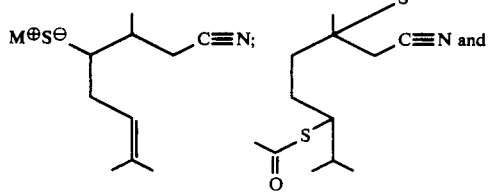

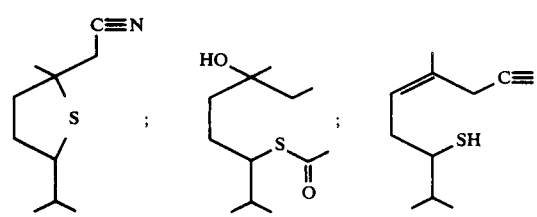

(wherein M is alkali metal), processes for preparing same, products produced by said processes as well as organoleptic uses of said products produced by said processes as well as the subgenus of compounds having the structures:

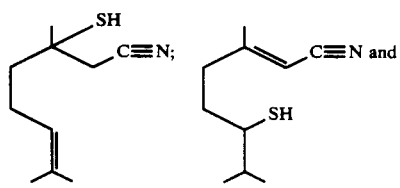

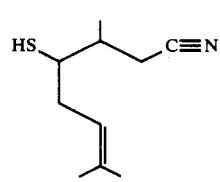

in augmenting or enhancing the aroma or taste of consumable materials.

Such consumable materials are perfume compositions, perfumed articles, perfumes, colognes, foodstuffs and chewing gums.

This invention also relates to the process for preparing the compounds having the structures;

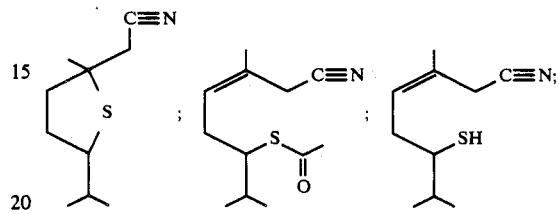

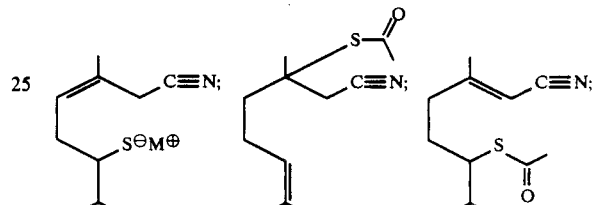

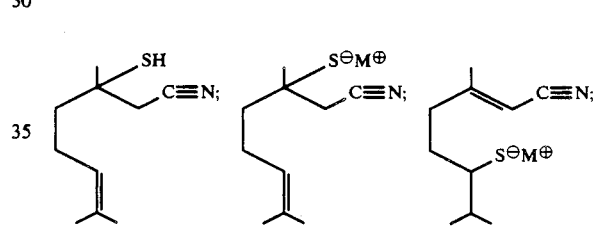

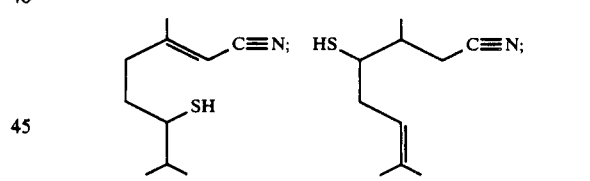

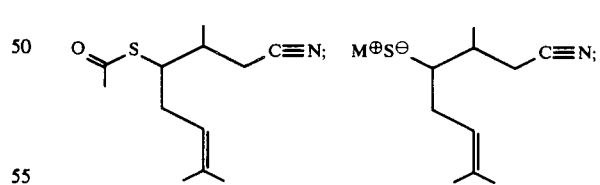

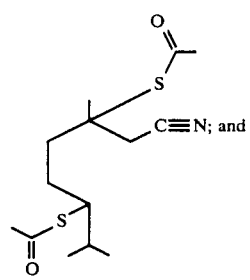

-continued
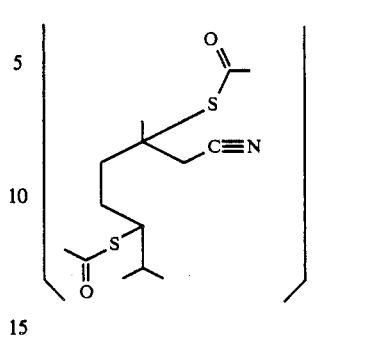
(wherein M is alkali metal) by means of reacting geranonitrile, either in the form of a mixture of compounds having the structures:
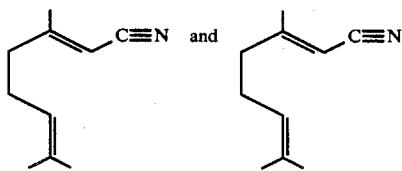
or (ii) in the form of the single compound having the structure:
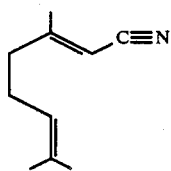
with thioacetic acid according to one of the following two reaction sequences:
(i)
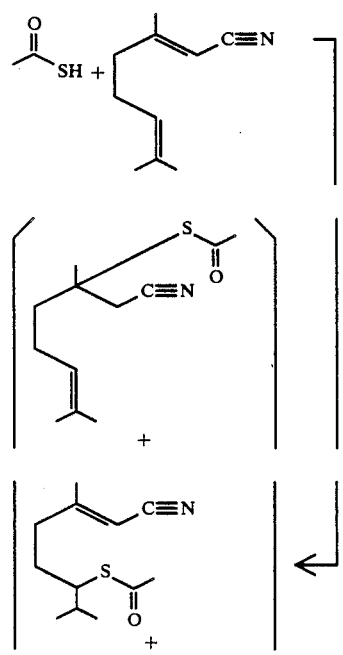
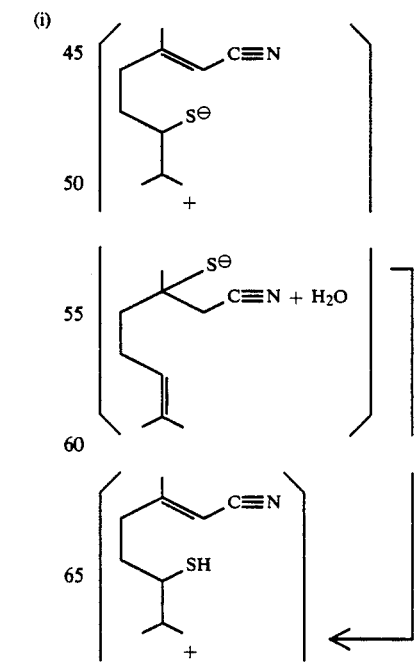
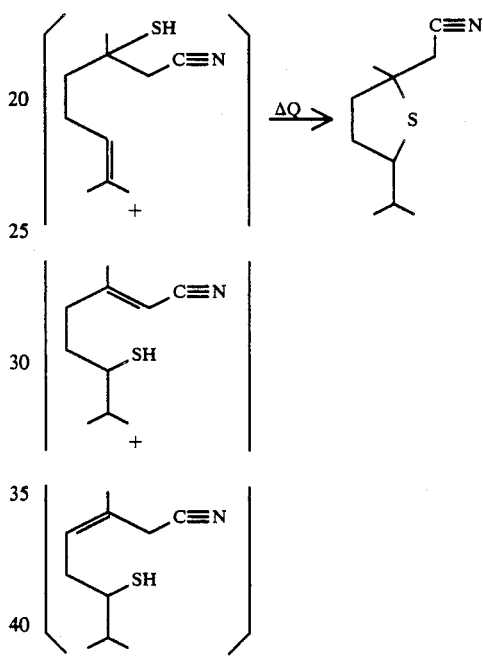

-continued
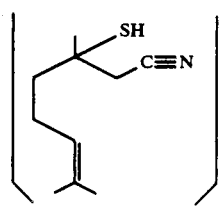
and
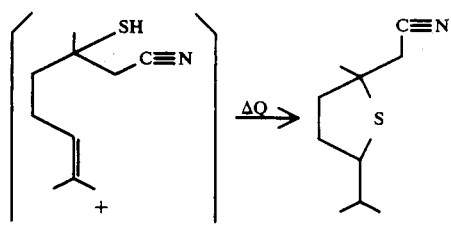
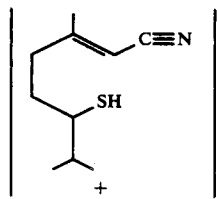
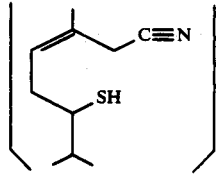
or
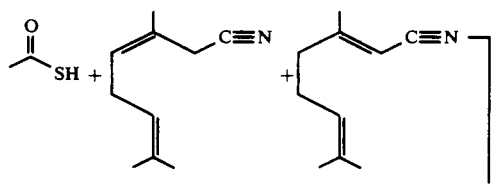
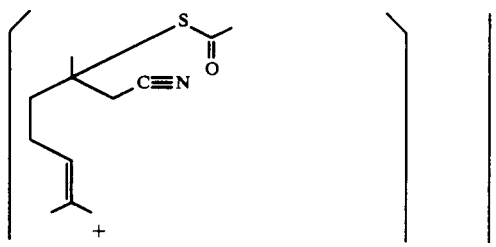
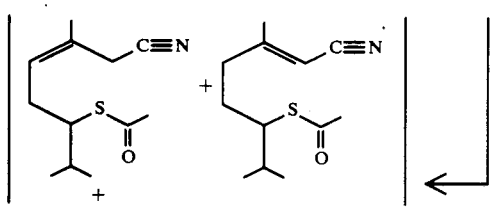
-continued
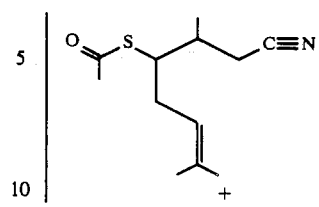
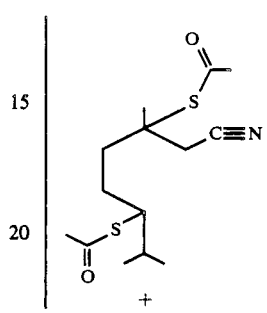
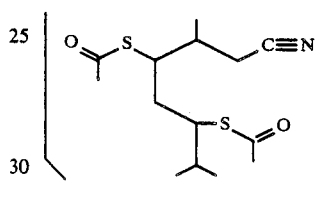
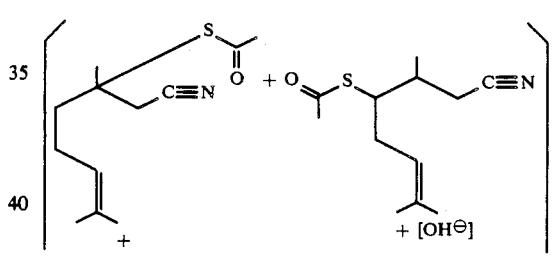
(ii)
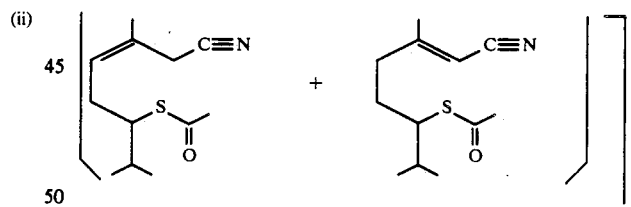
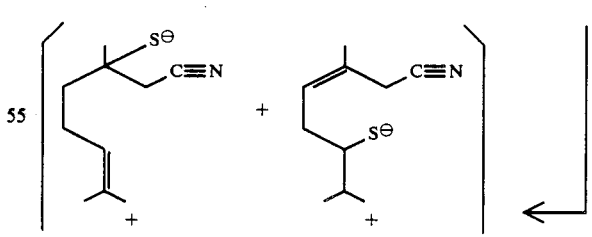
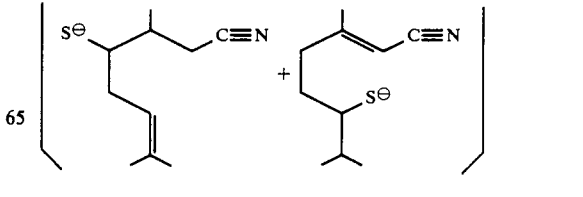

-continued
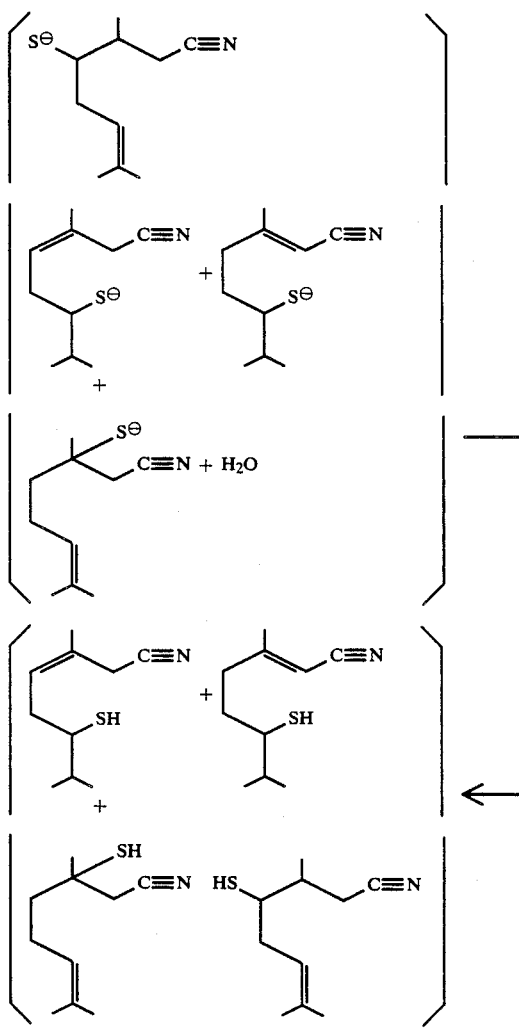
and
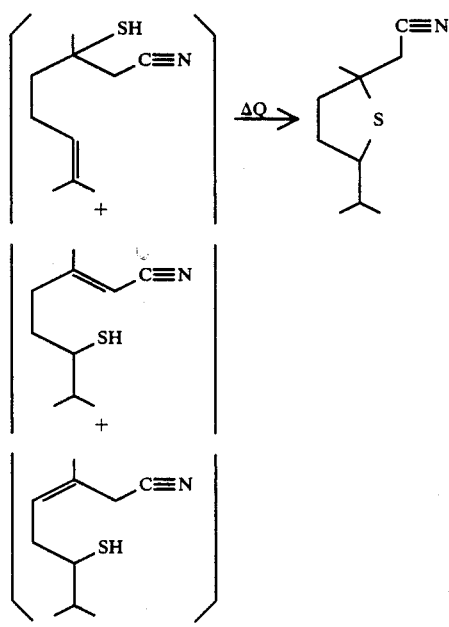
The reactions, to wit:
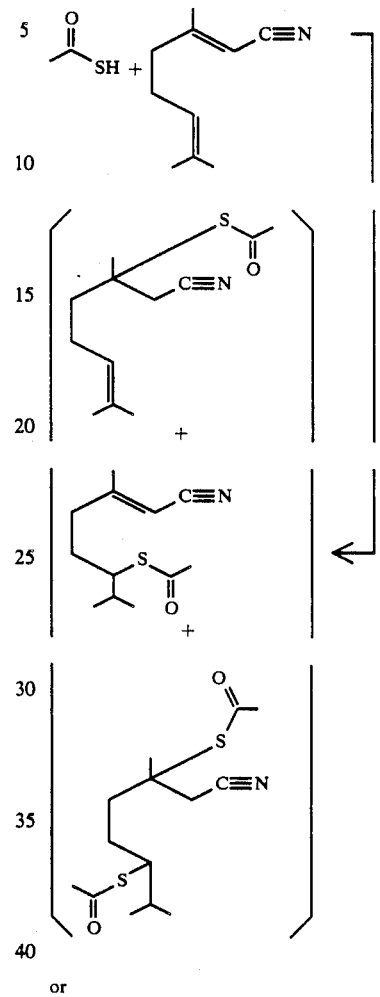
or
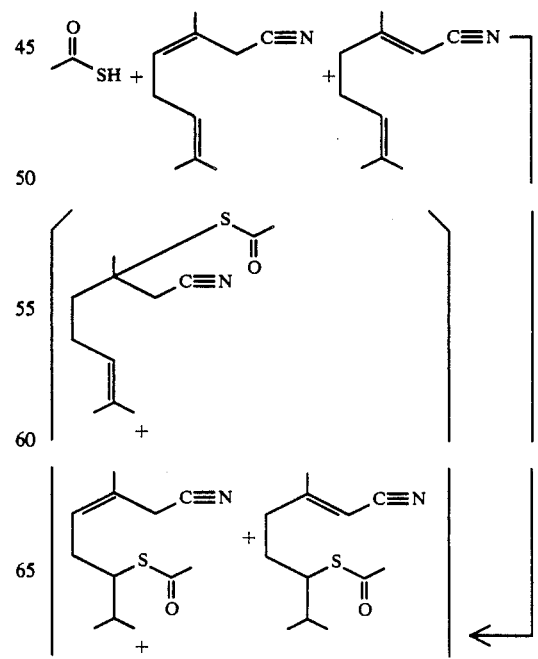

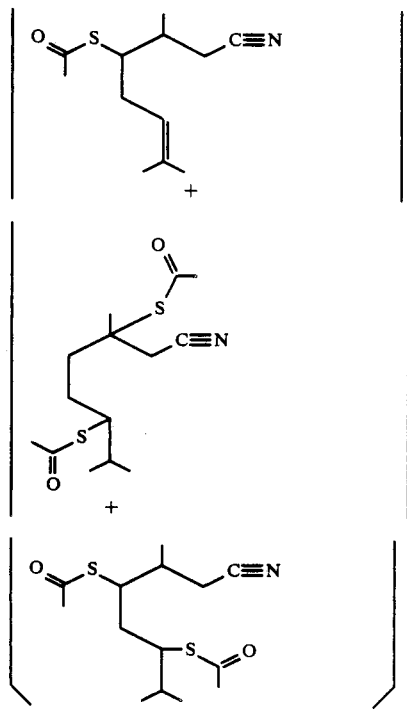

are carried out a temperature of 60°-80° C. over a period of between about 1 and about 5 hours. The mole ratio of geranonitrile, either (a) the mixture of compounds having the structures:

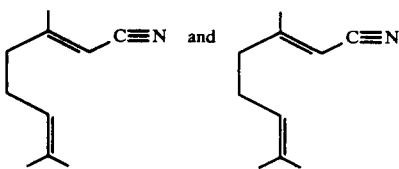

or (b) the single compound having the structure:

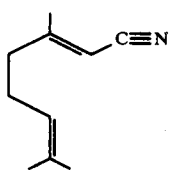

to thioacetic acid is between about 1:0.5 and about 0.5:1 with a slight excess of mixture of compounds having the structures:

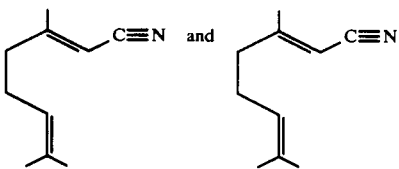

or the single compound having the structure:

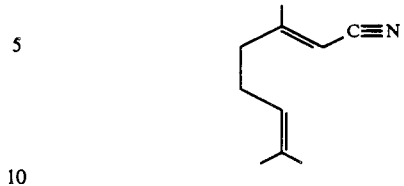

to thioacetic acid being preferred (e.g., 3:2.5).

At the end of the reaction, the reaction products having the structures;

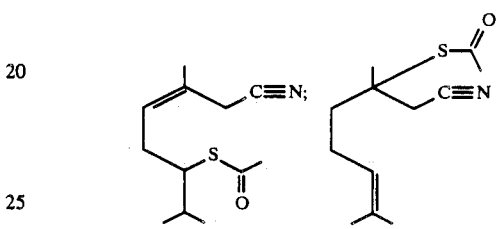

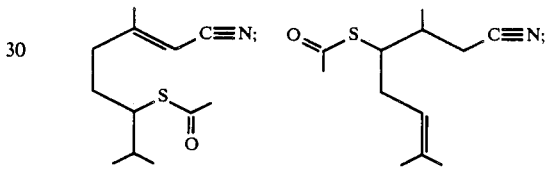

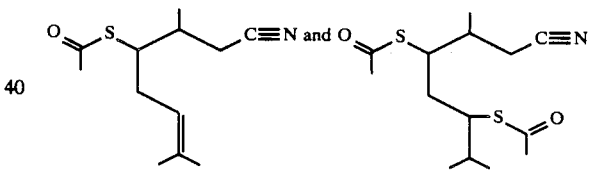

are washed with base (e.g., sodium bicarbonate, sodium hydroxide, potassium hydroxide or lithium hydroxide) giving rise to the following reactions:

(i)

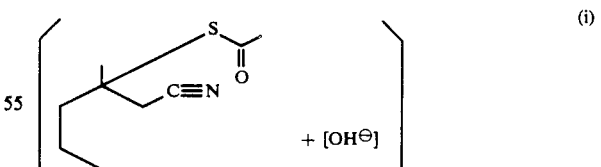
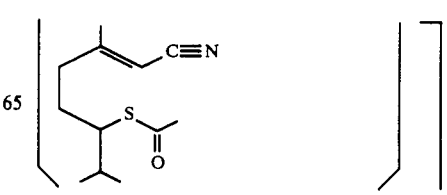

-continued
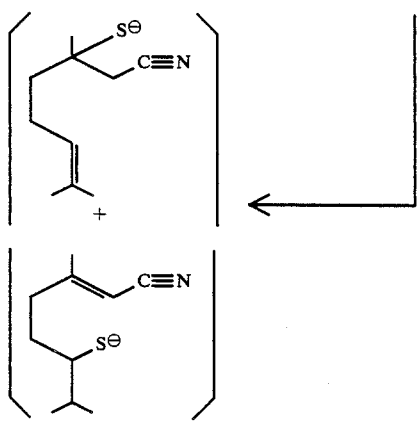
or
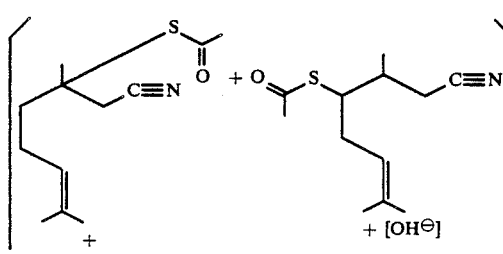
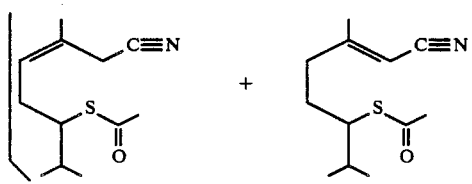
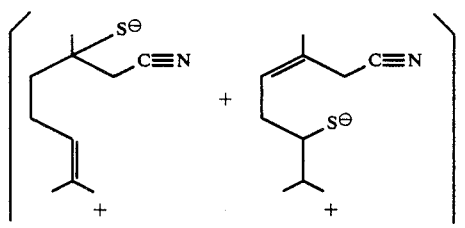
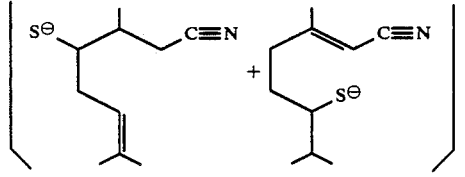
The compounds thus produced having the structures;
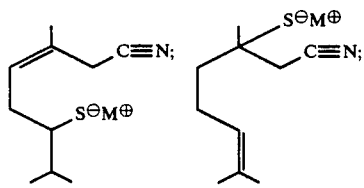
-continued
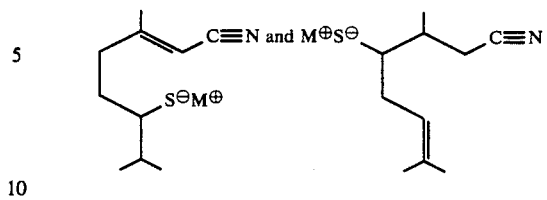
(wherein M represents alkali metal) on treatment with water according to one of the reactions:
(i)
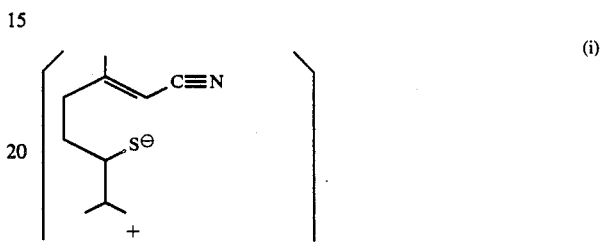
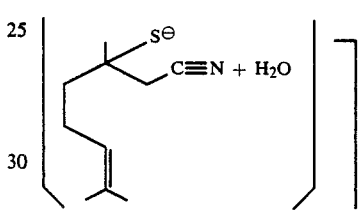
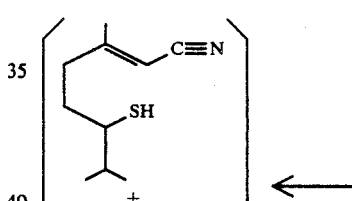
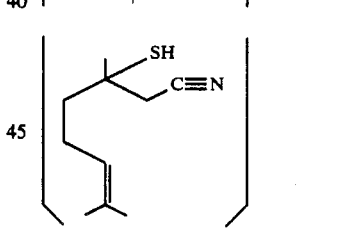
or
(ii)
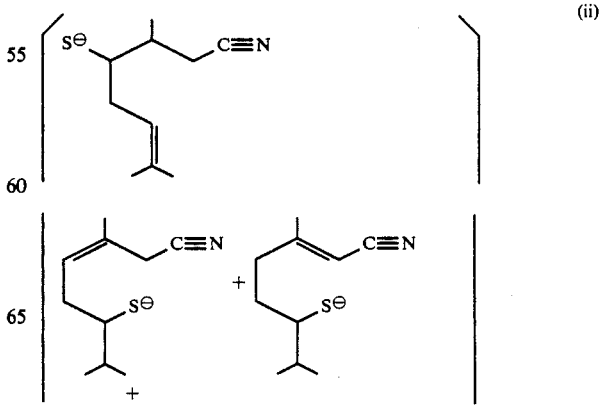

-continued

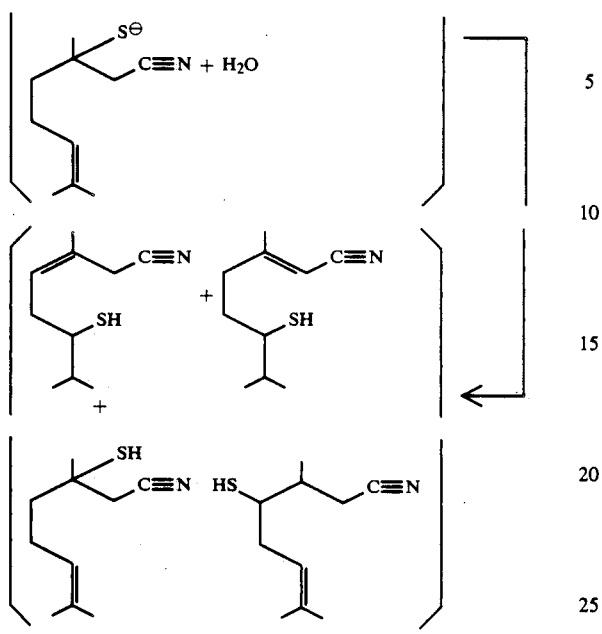

give rise to production of the compounds having the structures;

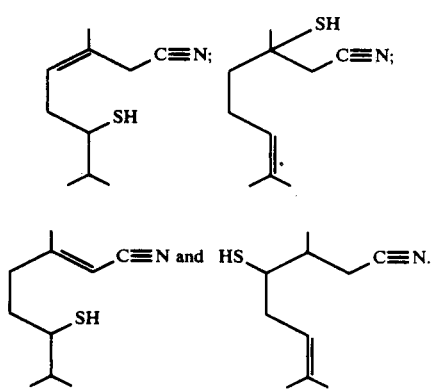

These compounds may be used "as is" for their organoleptic properties or the compounds having the structures:

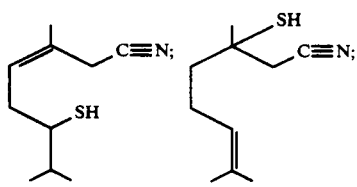

and

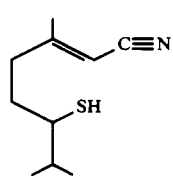

may be cyclized on heat treatment (e.g., during distillation) according to the reaction:

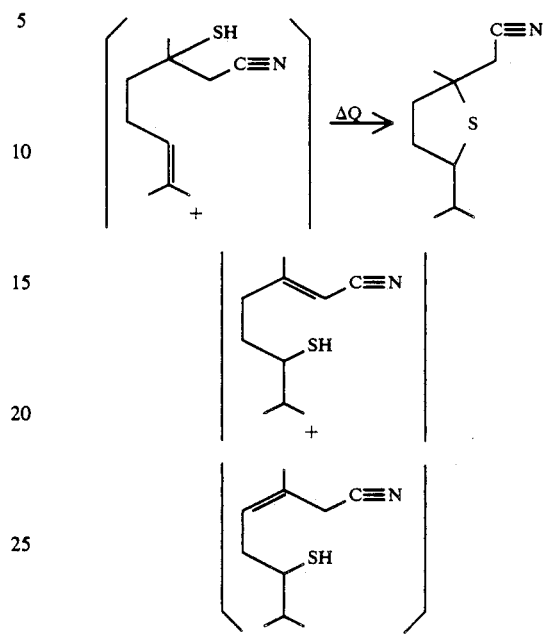

causing the compound having the structure;

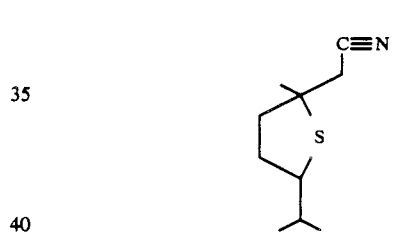

to be recovered which may be also shown as having the structure:

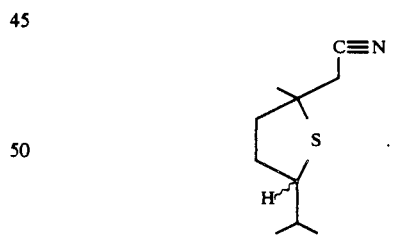

The compound having the structure:

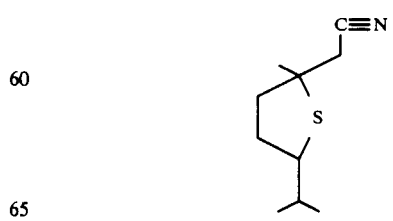

distills at 108° C. and 3 mm/Hg. pressure.
The compounds having the structures:

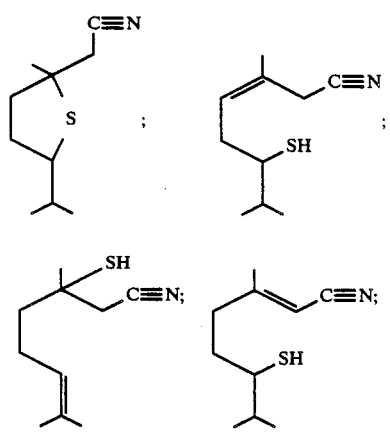

and

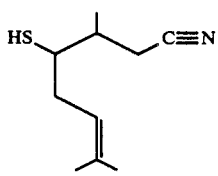

each have a natural buchu leaf, tomato leaf, herbaceous, basil, minty and grapefruit-like aroma with natural "ontiga", tomato leaf, minty and grapefruit-like undertones from a fragrance standpoint. From a flavor standpoint the compounds having the structures:

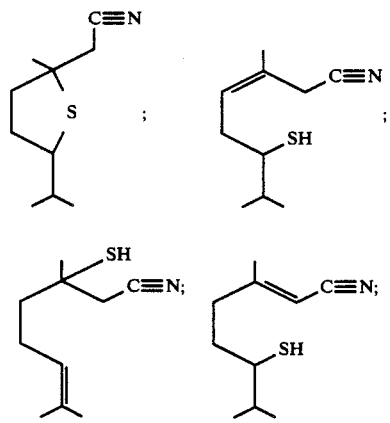

and

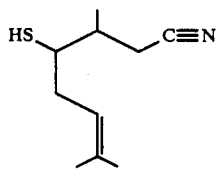

each has a green, minty, grapefruit-like and nootkatone aroma and taste profile.

The compounds having the structures:

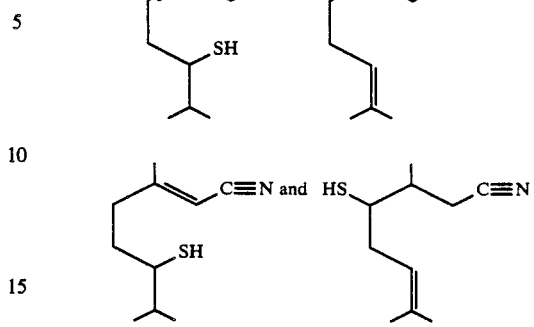

each have intensities and substantivities at least twofold (2×x) that of the compound having the structure;

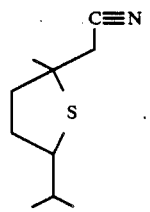

This invention also relates to a process for preparing the S(4-hdyroxy-1-isopropyl-4-methylhexyl) thioacetate having the structure:

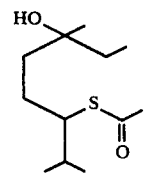

by reacting thioacetic acid having the structure;

with dihydrolinalool having the structure:

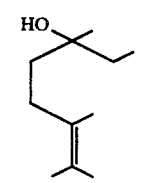

according to the reaction:

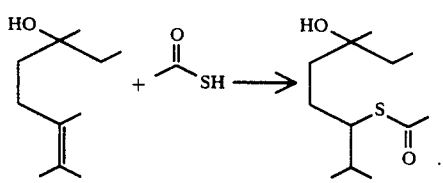

The reaction is carried out at a temperature in the range of from about 65° C. up to about 95° C. for a period of time of from about one hour up to about five hours. The mole ratio of dihydrolinalool having the structure:

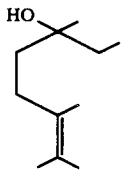

to thioacetic acid having the structure:

may range from about 0.5:1.5 up to about 1.5:0.5 with a preferred mole ratio of about 3.0 moles dihydrolinalool to 2.5 moles thioacetic acid.

The compound having the structure:

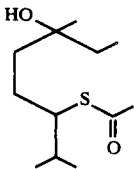

has a green, floral and rose aroma profile.

Table I set forth below indicates the organoleptic properties of materials produced according to the processes of our invention:

TABLE I

| Structure of Hydroxyl-and-Cyano-Substituted Sulfur-Containing Compound: | Organoleptic Properties |
|---|---|
| Tetrahydro-5-isopropyl-2-methyl-2-thiophene acetonitrile having the structure:<br>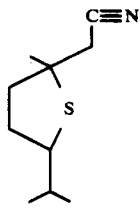produced according to Example I. | A natural buchu leaf, tomato leaf, herbaceous, basil, minty and grapefruit-like aroma profile with natural "ontiga", tomato leaf, minty and grapefruit-like undertones. |
| The compound having the structure:<br>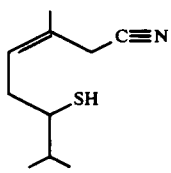 | A natural buchu leaf, tomato leaf, herbaceous, basil, minty and grapefruit-like aroma profile with natural "ontiga", tomato leaf, minty and grapefruit-like undertones having an intensity and substantivity twofold that of the compound having the structure: |

TABLE I-continued

| Structure of Hydroxyl-and-Cyano-Substituted Sulfur-Containing Compound: | Organoleptic Properties |
|---|---|
| 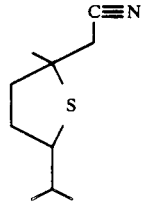produced according to Example I. | A natural buchu leaf, tomato leaf, herbaceous, basil, minty and grapefruit-like aroma profile with natural "ontiga", tomato leaf, minty and grapefruit-like undertones having an intensity and substantivity twofold that of the compound having the structure: |
| The compound having the structure:<br>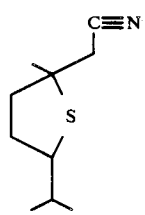produced according to Example I. | A natural buchu leaf, tomato leaf, herbaceous, basil, minty and grapefruit-like aroma profile with natural "ontiga", tomato leaf, minty and grapefruit-like undertones having an intensity and substantivity twofold that of the compound having the structure: |
| The compound having the structure:<br>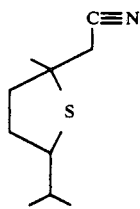produced according to Example I. | A natural buchu leaf, tomato leaf, herbaceous, basil, minty and grapefruit-like aroma profile with natural "ontiga", tomato leaf, minty and grapefruit-like undertones having an intensity and substantivity twofold that of the compound having the structure: |
| The compound having the structure:<br>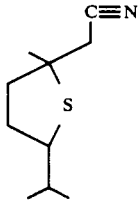 | |

TABLE I-continued

| Structure of Hydroxyl-and-Cyano-Substituted Sulfur-Containing Compound: | Organoleptic Properties |
|---|---|
| The compound having the structure: 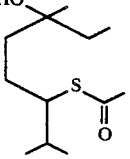 prepared according to Example II. | produced according to Example I. A green, floral and rose aroma profile. |

The organoleptically useful hydroxyl-and-cyano-substituted sulfur-containing compounds of our invention having the structures;

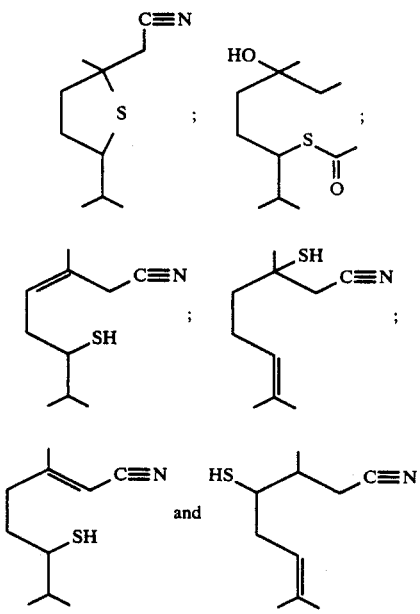

are useful as olfactory agents and can be incorporated into a wide variety of compositions each of which will be enhanced or augmented by their natural green, floral, rose, buchu leaf, tomato leaf, herbaceous, basil, minty and grapefruit-like aromas with natural tomato leaf, minty and grapefruit-like undertones.

The organoleptically useful hydroxyl-and-cyano-substituted sulfur-containing compounds of our invention can be added to perfume compositions as pure compounds or they can be added to mixtures of materials in fragrance imparting compositions to provide a desired fragrance character to a finished perfume material.

The perfume and fragrance compositions obtained according to this invention are suitable in a wide variety of perfumed articles and can also be used to enhance, modify or reinforce natural fragrance materials. It will thus be appreciated that the organoleptically useful hydroxyl-and-cyano-substituted sulfur-containing compounds of our invention is useful as an olfactory agent and fragrance.

The term "perfume composition" is used herein to mean a mixture of compounds including, for example, natural essential oils, synthetic essential oils, alcohols, aldehydes, ketones, esters, lactones, nitriles (other than the nitrile of our invention) and frequently hydrocarbons which are admixed so that the combined odors of the individual components produce a pleasant or desired fragrance. Such perfume compositions usually contain (a) the main note or "bouquet" or foundation stone of the composition, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials. Such perfume compositions of our invention can be used in conjunction with carriers, vehicles, solvents, dispersants, emulsifiers, surface active agents, aerosol propellants and the like.

In perfume compositions, the olfactory components contribute their particular olfactory characteristics but the overall effect of the perfume composition will be the sum of the effect of each ingredient. This, the organoleptically useful hydroxyl-and-cyano-substituted sulfur-containing compounds of our invention can be used to alter, augment, modify or enhance the aroma characteristics of a perfume composition or a perfumed article, for example, by highlighting or moderating the olfactory reaction contributed by another ingredient of the composition.

The amount of the organoleptically useful hydroxyl-and-cyano-substituted sulfur-containing compounds of our invention which will be effective in perfume compositions depends upon many factors including the other ingredients, the amounts and the effects which are desired. It has been found that perfume compositions containing as much as 40% or as little as 0.005% by weight of the organoleptically useful hydroxyl-and-cyano-substituted sulfur-containing compounds of this invention, or even less, can be used to impart a powerful, long-lasting, green, floral, rose, natural buchu leaf, tomato leaf, herbaceous, basil, minty and grapefruit-like aroma with natural "ontiga" tomato leaf, minty and grapefruit-like undertones to soaps, cosmetics and other products. The amount employed will depend upon considerations of cost, nature of the end product, the effect desired in the finished product and particular fragrance sought.

The organoleptically useful hydroxy-and-cyano-substituted sulfur-containing compounds of our invention as disclosed herein can be used alone in a fragrance modifying composition or in a perfume composition as an olfactory component in detergents (e.g., anionic, cationic, nonionic or zwitterionic solid or liquid detergents, and soaps, space deodorants; perfumed plastics; perfume compositions; colognes, bath preparations such as bath oils, bath salts; hair preparations such as lacquers, brilliantines, pomades and shampoos; fabric softener compositions, fabric softener articles such as BOUNCE ® (manufactured by the Procter & Gamble Company of Cincinnati, Ohio), cosmetic preparations such as creams, powders, deodorants, hand lotions, sun screens, powders such as talcs, dusting powders, face powders and the like. When the organoleptically useful hydroxyl-and-cyano-substituted sulfur-containing compounds of our invention is used in perfumed articles such as the foregoing, it can be used in amounts of 0.01% or lower and generally it is preferred not to use more than about 2% in the finished perfumed article since the use of too much will tend to unbalance the total aroma and will needlessly raise the cost of the article. Thus, in summary, in perfumed articles, the organoleptically useful hydroxyl-and-cyano-substituted sulfur-containing compounds may be used in the range of from about 0.01% up to about 2.0%.

When the organoleptically useful hydroxyl-and-cyano-substituted sulfur-containing compounds of our invention are used as food flavor adjuvants are used as food flavor adjuvants, or is used to augment or enhance the flavor or aroma characteristics of foodstuffs, the nature of the co-ingredients included with said organoleptically useful hydroxyl-and-cyano-substituted sulfur-containing compounds of our invention in formulating the product composition will also to augment the organoleptic characteristics of the ultimate foodstuff treated therewith.

As used herein in regard to flavors, the term "augment" in its various forms means "supplying or imparting flavor, character or note to otherwise bland, relatively tasteless substances or augmenting the existing flavor characteristics wherein natural flavor is deficient in some regard or supplementing the existing flavor impression to modify its quality, character or taste".

As used herein in regard to food flavors, the term "enhance" is used to mean the intensification of a flavor or aroma characteristic or note without the modification of the quality thereof. Thus "enhancement" of a flavor or aroma means that the enhancement agent does not add any additional flavor note.

As used herein the term "foodstuff" includes both solids and liquids and ingestible materials or chewable but non-ingestible materials such as chewing gum. Such materials usually do, but need not have nuritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the organoleptically useful hydroxyl-and-cyano-substituted sulfur-containing compounds of our invention, they should also be non-reactive with the organoleptically useful hydroxyl-and-cyano-substituted sulfur-containing compounds of our invention and "ingestibly acceptable" and thus, non-toxic or otherwise non-deleterious. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skin milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, beta,beta-dimethylacrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmin absolute, rose absolute, orris absolute, lemon essential oil, Bulgarian rose, yara yara, natural raspberry oil and vanilla; lactones; sulfides, e.g., methyl sulfide and other materials such as maltol, pulegone mercaptan, alpha-phellandrene, ethyl maltol, 2,2,4,4,6,6-hexamethyl-S-trithiane, acetoin and acetals, (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the organoleptically useful hydroxyl-and-cyano-substituted sulfur-containing compounds of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of the organoleptically useful hydroxyl-and-cyano-substituted sulfur-containing compounds of our invention employed in a particular instance can vary over a relatively wide range whereby to its desired organoleptic effects having reference to the nature of the product are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e, sufficient to alter the organoleptic characteristics of the parent composition, whether foodstuff per se of flavoring composition.

The use of insufficient quantities of the organoleptically useful hydroxyl-and-cyano-substituted sulfur-containing compounds of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of the organoleptically useful hydroxyl-and-cyano-substituted sulfur-containing compounds of our invention ranging from a small but effective amount, e.g., about 0.1 parts per million up to about 50 parts per million by weight based on total composition (more preferably, from about 0.2 ppm up to about 10 ppm) are suitable. Concentrations in excess of the maximum quantity stated are not normally recommended since they fail to prove commensurate with enhancement of organoleptic properties. In those instance wherein the organoleptically useful hydroxyl-and-cyano-substituted sulfur-containing compounds of our invention are added to the foodstuff as an integral component of a flavoring composition it is, of course, essential that the total quantity of flavoring composition employed be sufficient to yield an effective organoleptically useful hydroxyl-and-cyano-substituted sulfur-containing compounds of our invention in the foodstuff product.

Food flavoring compositions prepared in accordance with the present invention preferably contain the organoleptically useful hydroxyl-and-cyano-substituted sulfur-containing compounds of our invention in concentrations ranging from about 0.1% up to about 15% by weight based on the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the organoleptically useful hydroxyl-and-cyano-substituted sulfur-containing compounds of our invention with, for example, gum arabic, gum tragacanth, carageenan and the like, and thereafter spray-drying the resultant mixture whereby to obtain the particular solid product. Pre-prepared flavor mixed in powder form, e.g., a fruit flavored powder mix, is obtained by mixing the dried solid components, e.g., starch, sugar and the like, and the organoleptically useful hydroxyl-and-cyano-substituted sulfur-containing compounds of our invention in a dry blender until the requisite degree of uniformity is achieved.

It is presently preferred to combine with the organoleptically useful hydroxyl-and-cyano-substituted sulfur-containing compounds of our invention the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl perlargonate;
Methyl anthranilate;
Isoamyl acetate;
Isobutyl acetate;
Alpha-ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine(4-allyl-1,2,6-trimethoxy benzene);
Isoelemecine(4-propenyl-1,2,6-trimethoxybenzene);
2-(4-Hydroxy-4-methylpentyl)norbornadiene prepared according to U.S. Application for U.S. Pat. Ser. No. 461,703 filed on Apr. 17, 1974, now U.S. Pat. No. 3,886,289;
Natural blackcurrent juice;
Buchu leaf oil;
Alpha-phellandrene;
Cis-3-hexen-1-ol;
Terpinenol-4;
Ethyl maltol;
Methyl benzoate;
Benzaldehyde;
Coriander oil;
Alpha-ionone;
Ethyl heptanoate;
Ethyl anthranilate;
Cinnamic alcohol;
Amyl valerinate;

Cinnamyl propionate;
Rhodinyl acetate;
Methyl beta-hydroxy butyrate;
Ethyl beta-hydroxy butyrate;
2-Phenyl-3-carboethoxyfuran;
Cyclohexyl disulfide;
Grapefruit oil
Nootkatone;
Bergamot oil;
Citral;
Amyl alcohol;
5-Phenyl-4-pentenal;
5-Phenyl-2-pentenal;
Allyl caproate;
2-(n-Pentyl)thiazole;
2-(i-Butyl)thiazole;
2-(i-Propyl)thiazole;
2-(n-propyl)thiazole;
2-Phenyl-4-pentenal;
2-Phenyl-4-pentenaldimethylacetal;
Methional;
4-Methylthiobutanal;
2-Ethyl-3-acetylpyrazine;
Tetramethyl pyrazine;
2-Methyl pyrazine;
Trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thiobutanal-S-oxide;
Thioethanal-S-oxide;
Thiohexanal-S-oxide; and
Propyl propene thiosulfonate.

The following Examples I(A), I(B) and II are given to illustrate methods of preparing the organoleptically useful hydroxyl-and-cyano-substituted sulfur-containing compounds of our invention. The examples following Example II set forth methods whereby the organoleptically useful hydroxyl-and-cyano-substituted sulfur-containing compounds of our invention are utilized for their organoleptic properties.

It will be understood that these examples are illustrative and the invention is not to be considered as restricted thereto except as indicated in the appended claims.

EXAMPLE I(A)

Preparation of Cyano-Substituted Sulfur-Containing Compounds

Reactions:

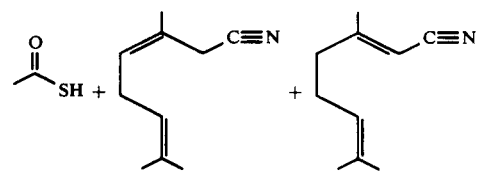

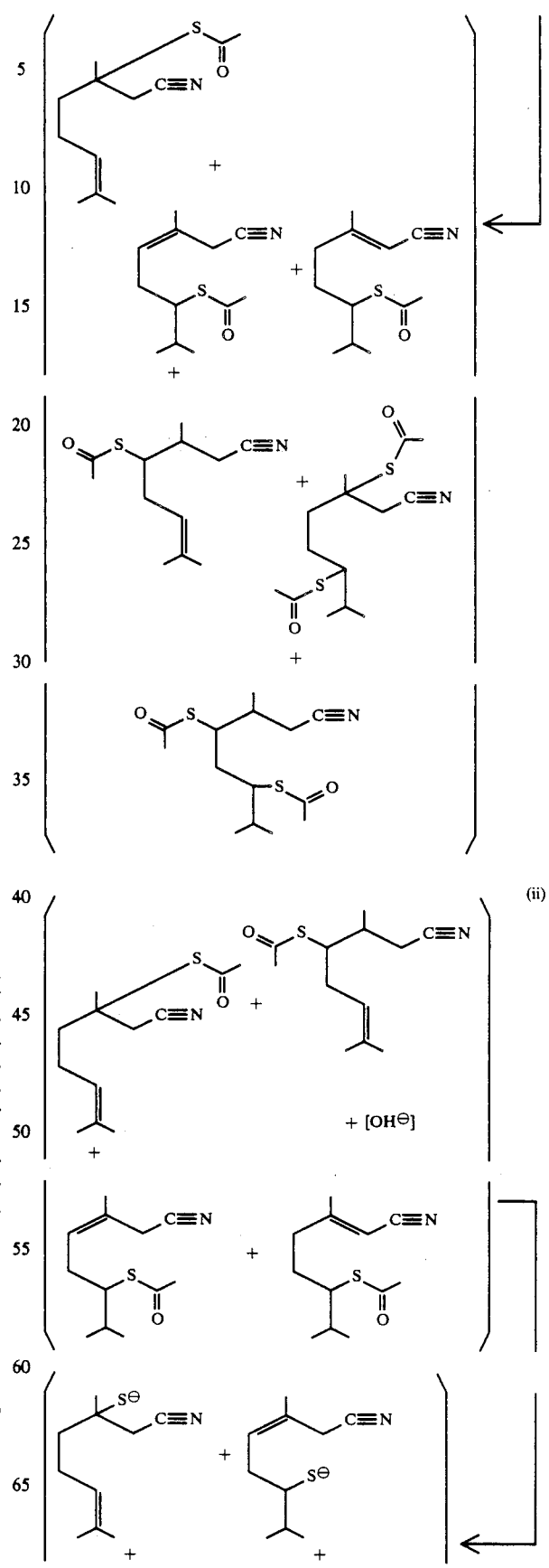

-continued

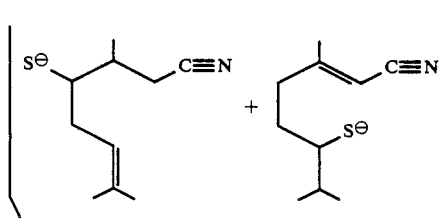

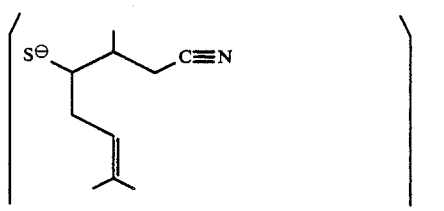

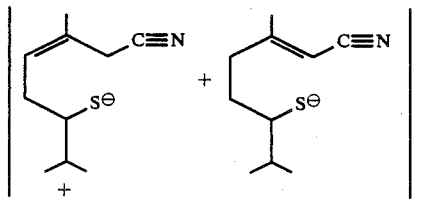
+ H₂O

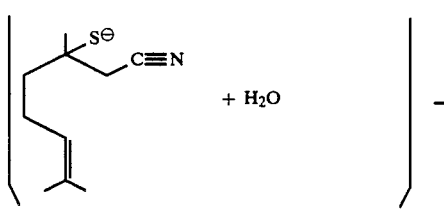

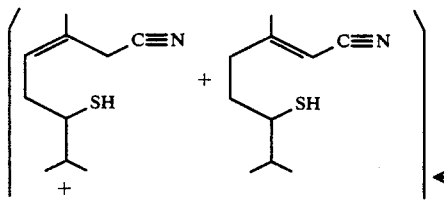

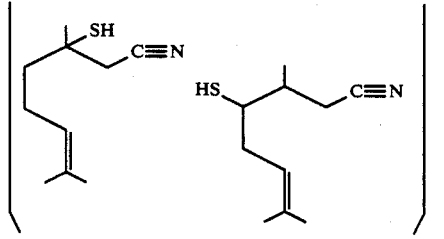

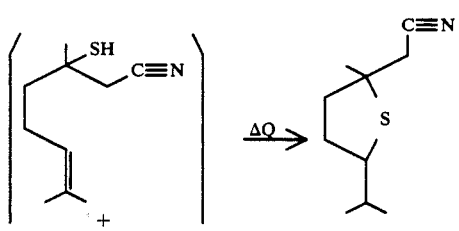

-continued (iii)
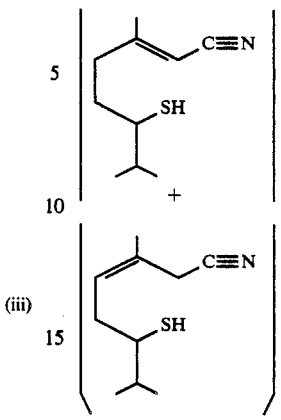

Into a 1 liter reaction vessel equipped with thermometer, stirrer, condenser and heating mantle is placed 455.0 grams (3.0 moles) of geranonitrile, a mixture of compounds having the structures:

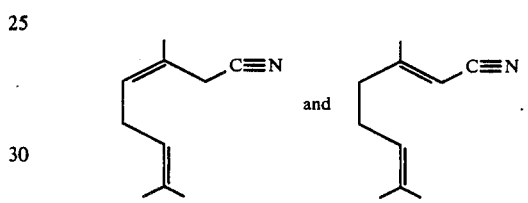

The geranonitrile is heated with stirring to 65° C. Dropwise, over a period of 60 minutes, while maintaining the reaction L temperature at 65° C., 190.0 grams (2.5 moles) of thioacetic acid is added to the reaction mass.

The reaction mass is then stirred at 65°–70° C. of one hour. The reaction mass is then heated and maintained at 70°–75° C. for a period of 1.25 hours causing the reaction:

(iv)
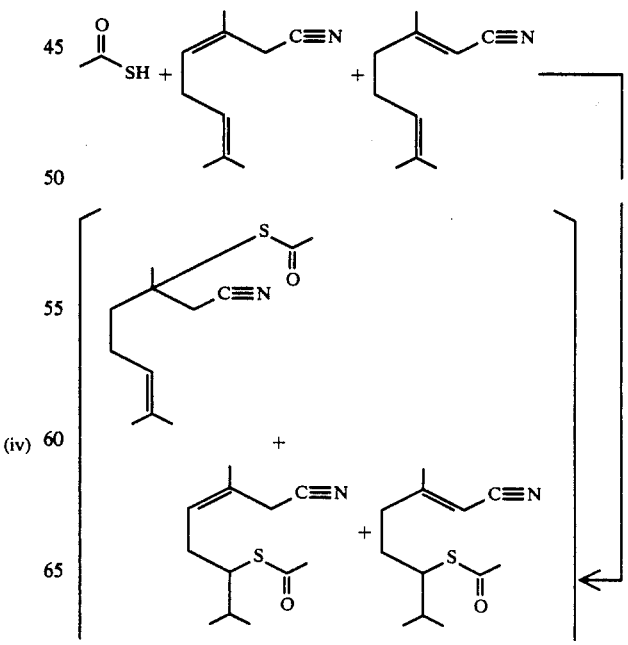

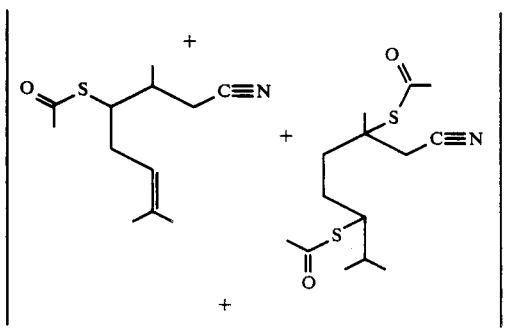

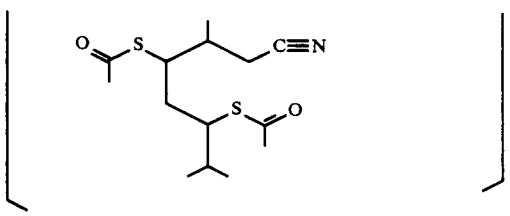

to take place.

The reaction mass is then cooled and 200 cc toluene is added thereto. The organic layer is separated from the aqueous phase and the organic layer is washed with one 200 cc portion of 20% aqueous sodium hydroxide causing the reactions:

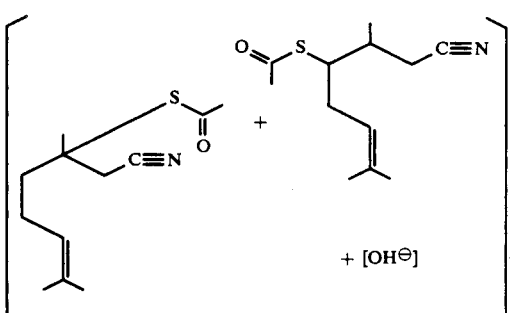

+ [OH⁻]

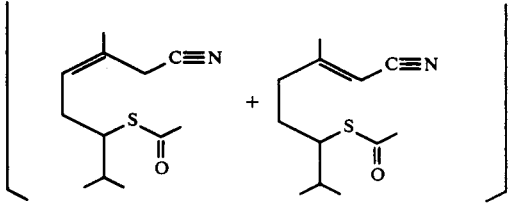

+

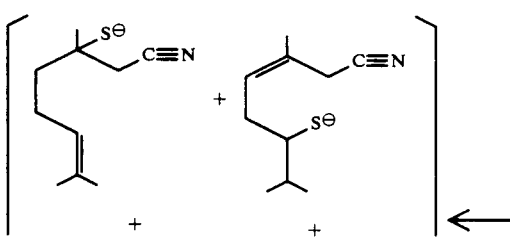

+

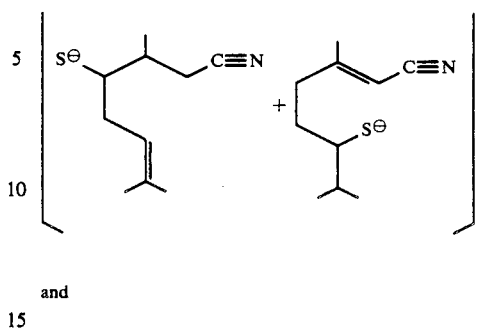

and

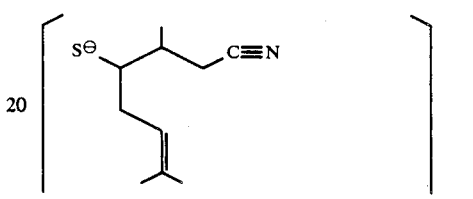

+

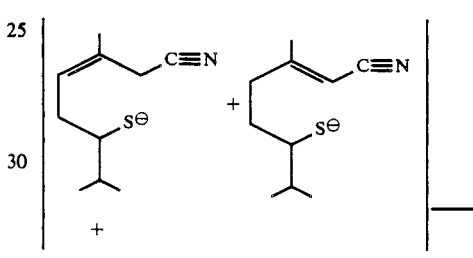

+

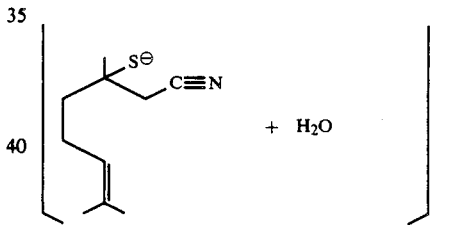

+ H₂O

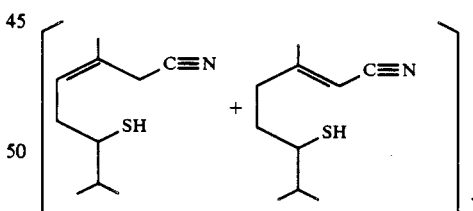

+

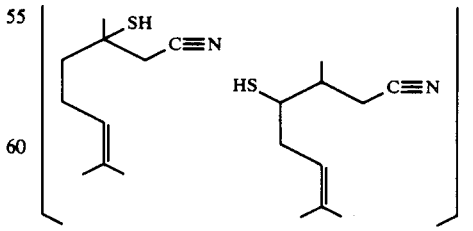

to take place.

The resulting washed product is then distilled on a 6" stone packed column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/100 | 120/125 | 3.0/3.0 | 15.0 |
| 2 | 100 | 135 | 3.5 | 15.0 |
| 3 | 105 | 145 | 3.5 | 40.0 |
| 4 | 105 | 160 | 3.5 | 50.0 |
| 5 | 108 | 175 | 3.5 | 60.0 |
| 6 | 108 | 177 | 3.0 | 30.0 |
| 7 | 108 | 179 | 3.0 | 45.0 |
| 8 | 108 | 181 | 3.0 | 20.0 | whereby the reaction:

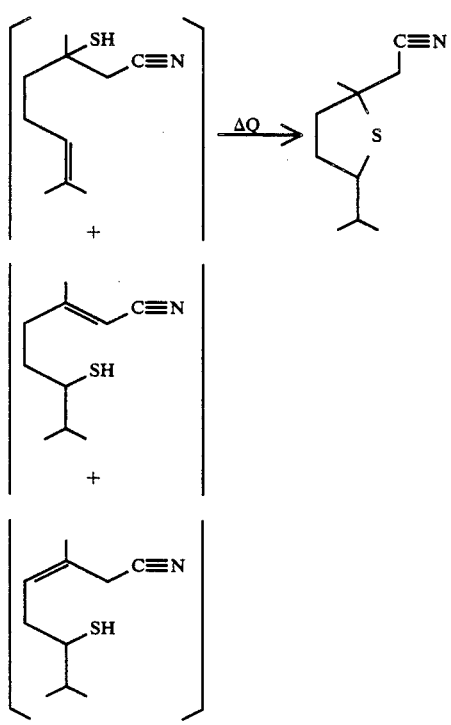

takes place.

The result distillation product is then bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/95 | 110/141 | 2.5/2.5 | 10.0 |
| 2 | 95 | 150 | 2.5 | 30.0 |
| 3 | 95 | 150 | 2.5 | 5.0 |
| 4 | 108 | 158 | 2.5 | 30.0 |
| 5 | 108 | 165 | 2.5 | 24.0 |
| 6 | 108 | 165 | 2.5 | 29.0 |
| 7 | 108 | 170 | 2.5 | 27.0 |
| 8 | 108 | 195 | 2.8 | 36.0. |

FIG. 1 is the GLC profile for the crude reaction product. The peak indicated by reference numeral 10 is the peak for the compound having the structure:

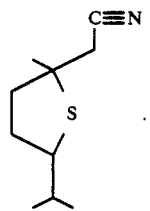

FIG. 2 is the GLC profile for fraction 6 of the second distillation (Conditions: SE-30 column programmed at 100°-220° C. at 8° C. per minute). The peak indicated by reference numeral 20 is the peak for the compound having the structure:

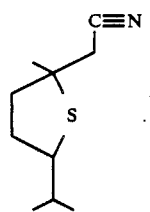

FIG. 3 is the NMR spectrum for the compound having the structure;

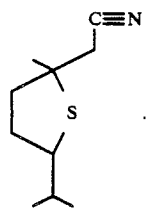

FIG. 4 is IR spectrum for the compound having the structure:

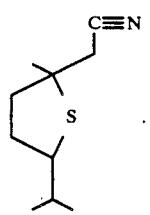

The compound having the structure:

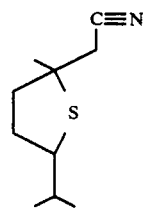

has a natural natural buchu leaf, tomato leaf, herbaceous, basil, minty and grapefruit-like aroma with natural "ontiga", tomato leaf, minty and grapefruit-like undertones from a fragrance standpoint.

From a flavor standpoint the compound having the structure:

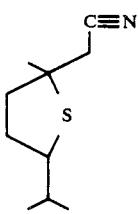

has a green, minty, grapefruit-like and nootkatone-like aroma and taste profile.

The compounds having the structures;

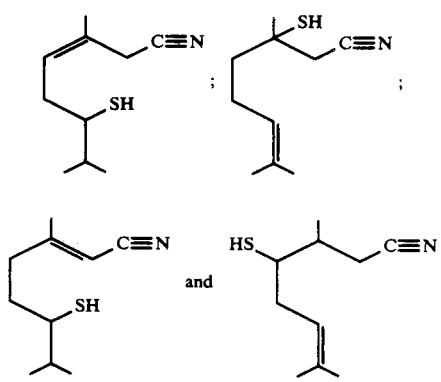

each has a natural buchu leaf, tomato leaf, herbaceous, basil, minty and grapefruit-like aroma with natural "ontiga", tomato leaf, minty and grapefruit-like undertones from a fragrance standpoint, twofold the intensity and substantivity of the compound having the structure:

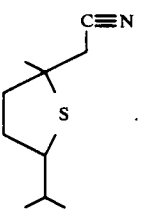

From a flavor standpoint each of the compounds having the structures;

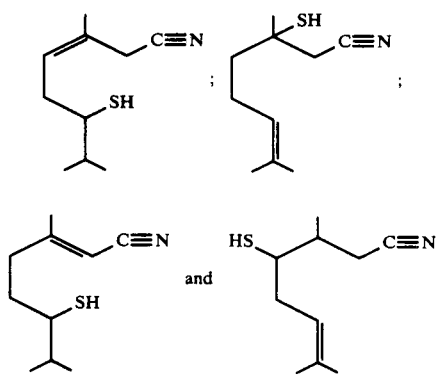

each has a green, minty, grapefruit-like and nootkatone-like aroma and taste profile twofold the intensity of the compound having the structure:

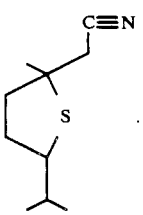

EXAMPLE I(B)

Preparation of Cyano-Substituted Sulfur-Containing Compounds

Reactions:

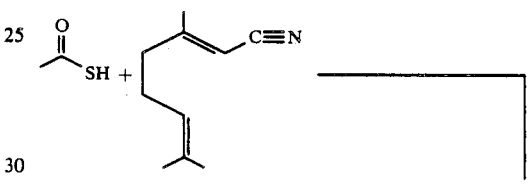

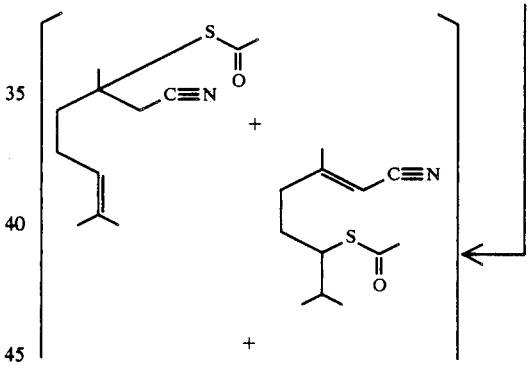

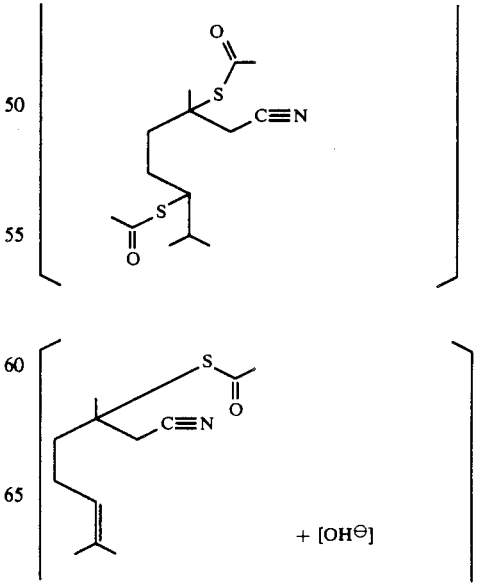

+ [OH⁻]

-continued

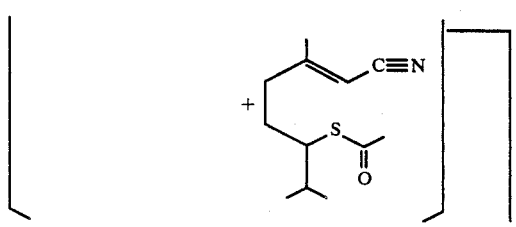

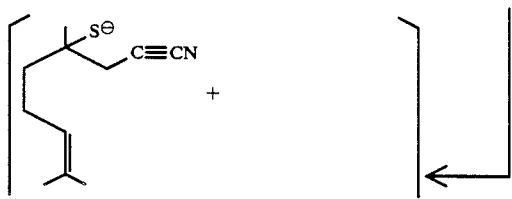

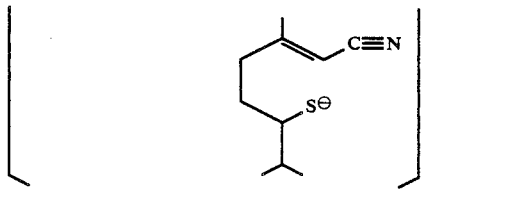

+ H₂O

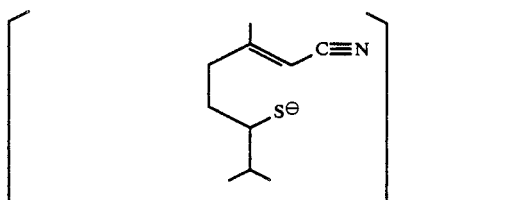

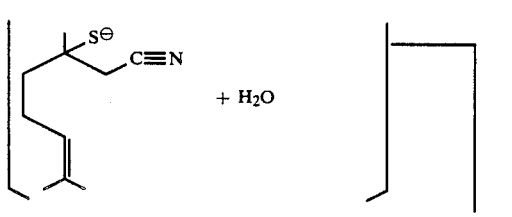

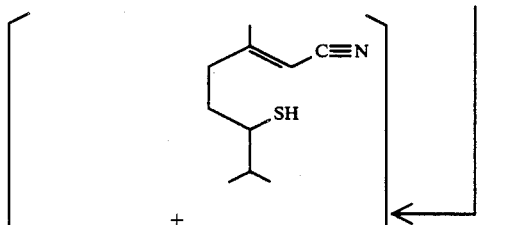

and

-continued

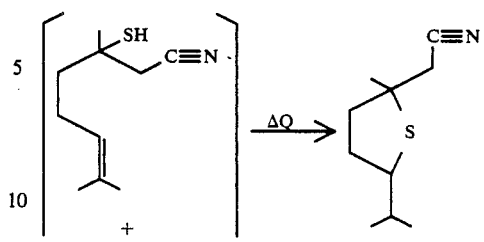

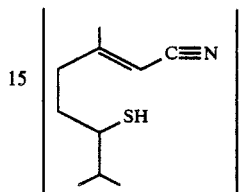

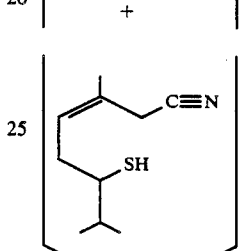

Into a 1 liter reaction vessel equipped with thermometer, stirrer, condenser and heating mantle is placed 455.0 grams (3.0 moles) of geranonitrile, the compound having the structure:

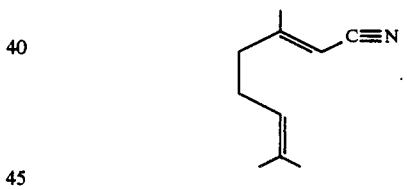

The geranonitrile is heated with stirring to 65° C.

Dropwise, over a period of 60 minutes, while maintaining the reaction temperature at 65° C., 190.0 grams (2.5 moles) of thioacetic acid is added to the reaction mass.

The reaction mass is then stirred at 65°-70° C. for one hour.

The reaction mass is then heated and maintained at 70°-75° C. for a period of 1.25 hours causing the reaction:

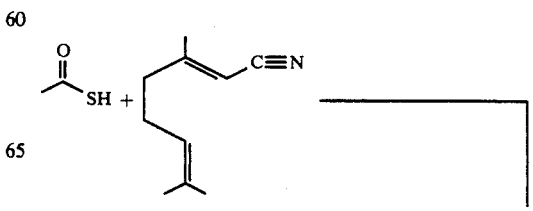

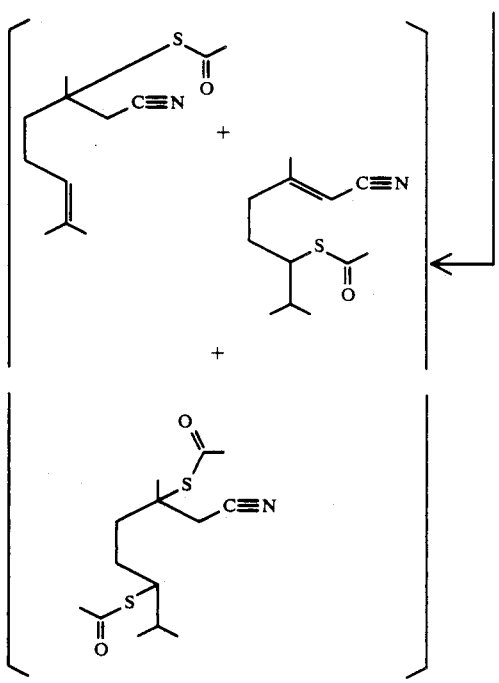

to take place.

The reaction mass is then cooled and 200 cc toluene is added thereto. The organic layer is separated from the aqueous phase and the organic layer is washed with one 200 cc portion of 20% aqueous sodium bicarbonate causing the reactions:

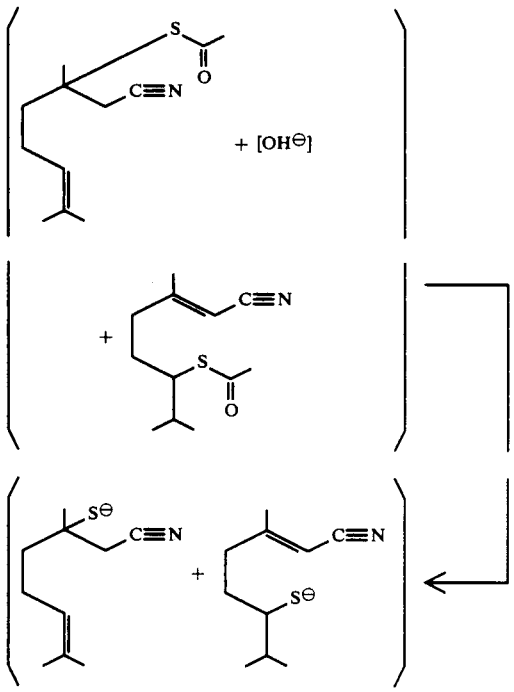

and

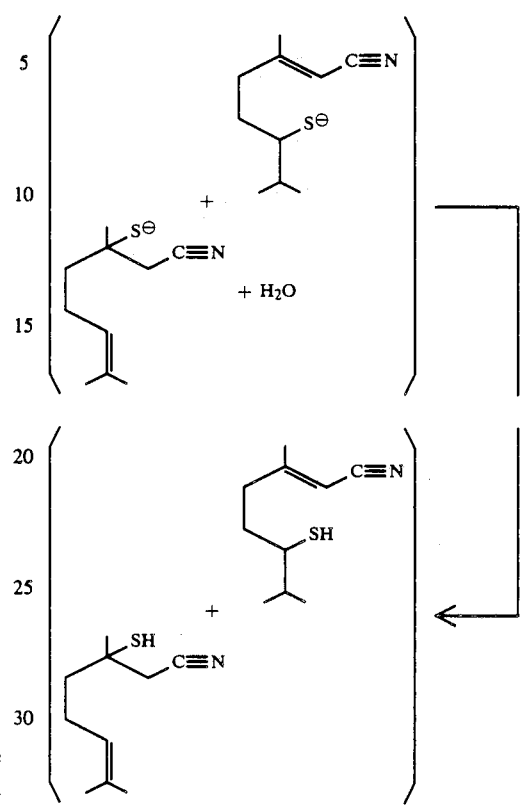

to take place.

The resulting washed product is then distilled on a 6" stone packed column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/100 | 120/125 | 3.0/3.0 | 15.0 |
| 2 | 100 | 135 | 3.5 | 15.0 |
| 3 | 105 | 145 | 3.5 | 40.0 |
| 4 | 105 | 160 | 3.5 | 50.0 |
| 5 | 108 | 175 | 3.5 | 60.0 |
| 6 | 108 | 177 | 3.0 | 30.0 |
| 7 | 108 | 179 | 3.0 | 45.0 |
| 8 | 108 | 181 | 3.0 | 20.0 | whereby the reaction:

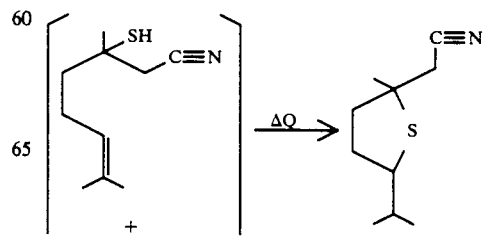

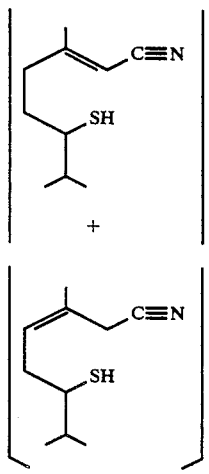

takes place.

The resulting distillation product is then bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/95 | 110/141 | 2.5/2.5 | 10.0 |
| 2 | 95 | 150 | 2.5 | 30.0 |
| 3 | 95 | 150 | 2.5 | 5.0 |
| 4 | 108 | 158 | 2.5 | 30.0 |
| 5 | 108 | 165 | 2.5 | 24.0 |
| 6 | 108 | 165 | 2.5 | 29.0 |
| 7 | 108 | 170 | 2.5 | 27.0 |
| 8 | 108 | 195 | 2.8 | 36.0. |

FIG. 5 is the GLC profile for the sodium bicarbonate washed crude product. The peaks indicated by reference numeral 150 are the peaks for the compounds having the structures;

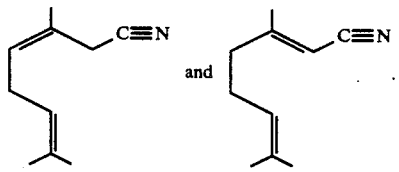

The peak indicated by reference numeral 152 is the peak for the compound having the structure;

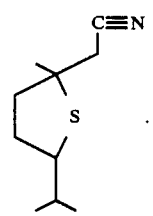

The peaks indicated by reference numeral 153 are the peaks for the compounds having the structures;

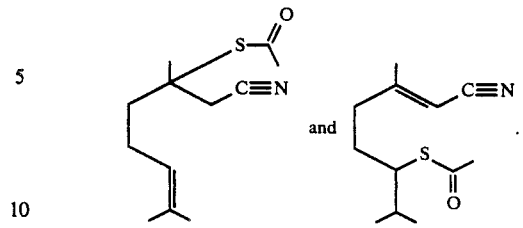

The peak indicated by reference numeral 154 is the peak for the compound having the structure;

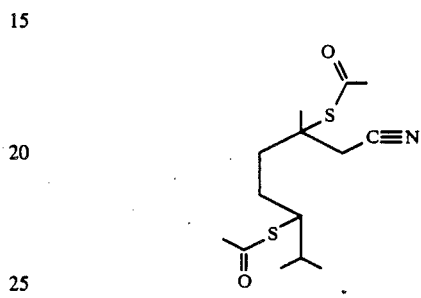

FIG. 6 is the GLC profile for the water washed crude reaction product.

The peaks indicated by reference numeral 160 are the peaks for the compounds having the structures:

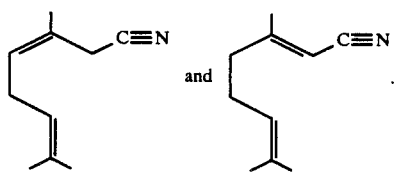

The peak indicated by reference numeral 162 is the peak for the compound having the structure;

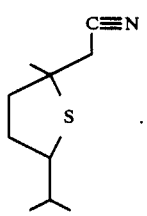

The peaks indicated by reference numeral 163 are the peaks for the compounds having the structures;

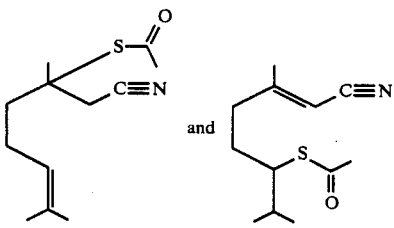

The Compounds having the structures;

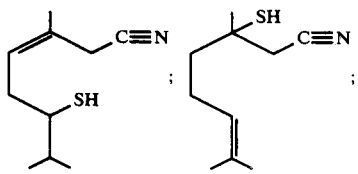

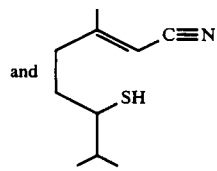

each has a natural buchu leaf, tomato leaf, herbaceous, basil, minty and grapefruit-like aroma with natural "ontiga", tomato leaf, minty and grapefruit-like undertones from a fragrance standpoint, with an intensity twofold that of the compound having the structure:

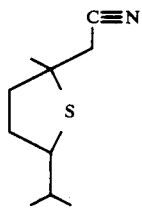

and a substantivity twofold that of the compound having the structure:

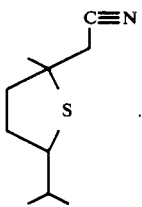

From a flavor standpoint the compounds having the structures:

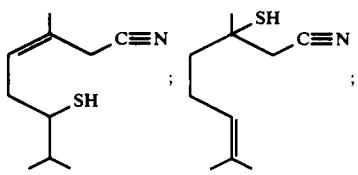

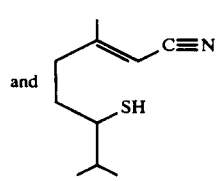

each has a green, minty, grapefruit-like and nootkatone-like aroma and taste profile approximately twice the intensity of the compound having the structure:

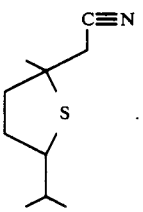

EXAMPLE II

Preparation of
S(4-Hydroxy-1-Isopropyl-4-Methylhexyl) Thioacetate

Reaction:

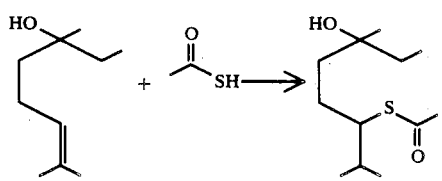

Into a 1 liter reaction vessel equipped with stirrer, thermometer, reflux condenser and heating mantle is placed 468.0 grams (3.0 moles) of dihydrolinalool having the structure:

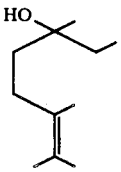

The dihydrolinalool is heated to 65° C. with stirring. While maintaining the dihydrolinalool at 65° C., dropwise over a period of one hour, thioacetic acid having the structure:

is added to the reaction mass. After addition of the thioacetic acid, the reaction mass is maintained at 65°–70° C. for a period of one hour. The reaction mass is then heated to 95°–90° C. for a period of one hour with stirring.

The reaction mass is then cooled and washed with two 200 cc portions of 20% aqueous sodium hydroxide.

The resulting product is distilled on a 4" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 75/92 | 80/90 | 3.8/3.8 | 200.0 |
| 2 | 98 | 105 | 3.5 | 200.0 |
| 3 | 125 | 145 | 3.5 | 41.0 |
| 4 | 150 | 220 | 3.5 | 280.0 |

The resulting product has the structure:

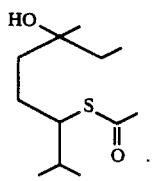

FIG. 5 is the GLC profile for the crude reaction product (Conditions: SE-30 column programmed at 100°–220° C. at 8° C. per minute). The peak indicated by reference numeral 50 is the peak for the compound having the structure:

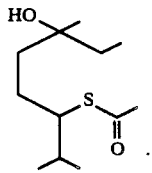

FIG. 6 is the GLC profile for fraction 4 of the distillation product of the reaction product of this example. The peak indicated by reference numeral 60 is the peak for the compound having the structure:

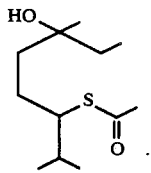

FIG. 7 is the NMR spectrum for the compound having the structure:

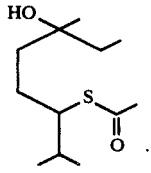

FIG. 8 is the infra-red spectrum for the compound having the structure:

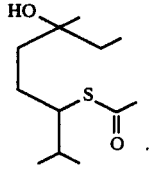

EXAMPLE III(A)

Impregnated Plastics and Air Fresheners

Scented polyethylene pellets having pronounced natural buchu leaf, tomato leaf, herbaceous, basil, minty and grapefruit-like aromas with natural "ontiga" tomato leaf, minty and grapefruit-like undertones are prepared as follows:

75 Pounds of polyethylene having a melting point of about 220° F. is heated to about 230° F. in a container of the kind illustrated in FIGS. 11 and 12. 12.5 Pounds of tetrahydro-5-isopropyl-2-methyl-2-thiophene acetonitrile having the structure:

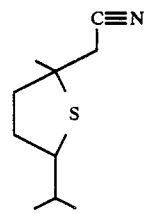

prepared according to Example I, supra, are then quickly added to the liquified polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the tetrahydro-5-isopropyl-2-methyl-2-thiophene acetonitrile containing material through the orifices 234 (whereby such material exits through orifices 234). The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼ in width×3″ in length and employed in standard air freshening apparatus.

On operation of the standard air freshening apparatus is a room air freshener, after 4 minutes, the room has an aesthetically pleasing aroma as set forth, supra.

EXAMPLE II(B)

Treated Plastics and Air Freshener

100 Pounds of polypropylene are heated to about 300° F. 15 Pounds of tetrahydro-5-isopropyl-2-methyl-2-thiophene acetonitrile prepared according to Example I are added to the liquified polypropylene. The procedure is carried out in the apparatus shown in FIGS. 11 and 12. After mixing for about 8 minutes, the valve "V" is opened to allow the exit of polypropylene mixture which has been treated with the tetrahydro-5-isopropyl-2-methyl-2-thiophene acetonitrile whereby solid pellets having pronounced aromas described as "natural buchu leaf, tomato leaf, herbaceous, basil, minty and grapefruit-like with natural "ontiga", tomato leaf, minty and grapefruit-like undertones" are formed on the conveyor. The pellets thus obtained are then admixed with about 20 times their weight of unscented polypropylene and untreated polypropylene and the mixture is heated and molded into "spaghetti" tows. The "spaghetti" tows are cut into small cylinders approximately 0.1 inches in length×0.2 inches in diameter. The cylinders have strong and pleasant aromas as described, supra.

The cylinders are used in standard air freshening apparatus to produce aesthetically pleasing aromas as set forth, supra, with no foul odors in environments surrounding the air freshener apparatus.

A portion of the cylinders are ground into small particles to be used in the deodorant stick of Example III(C).

EXAMPLE III(C)

Deodorant Stick

A deodorant stick composition is prepared containing the following materials:

| Ingredients | Parts by Weight |
|---|---|
| Propylene Glycol | 65.00 |
| Sodium stearate | 7.00 |
| Distilled water | 23.75 |
| IRGSAN ® DP-300 (2,4,4-trichloro-2'-hydroxy diphenyl ether, manufactured by the Ciba Geigy Chemical Company and the trademark of the Ciba Geigy Chemical Company of Hastings on Hudson, New York) | 0.25 |
| Ground polymer containing tetrahydro-5-isopropyl-2-methyl-2-thiophene acetonitrile produced according to Example III(B), supra. | 4.00 |

The ingredients are combined without the ground polymer and are heated to 75° C. These ingredients are mixed and continued to be heated until the sodium stearate has dissolved. The resulting mixture is cooled to 40° C. and the ground fragrance-containing polymer is added and mixed at 40° C. until a suspension is formed. The resulting suspension is cooled and formed into sticks and the deodorant sticks exhibit a pleasant fresh green aroma when utilized in the axillary areas of a human being.

EXAMPLE III(D)

Impregnated Plastics and Air Fresheners

Scented polyethylene pellets having a pronounced green, floral and rose aroma are prepared as follows:

75 Pounds of polyethylene having a melting point of about 220° F. is heated to about 230° F. in a container of the kind illustrated in FIGS. 11 and 12. 12.5 Pounds of one or a mixture of mercaptans having the structures:

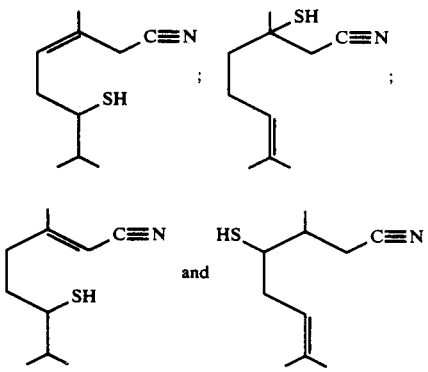

prepared according to Example I are then quickly added to the liquified poly- ethylene. The lid 228 is put in place and the agitating means 273 are actuated. The temperature is maintained at about 225° F. and the mixing is continued for about 15 minutes. The valve "V" is then opened to allow flow of the molten polyethylene enriched with the mercaptan-containing material through the orifices 234 whereby such material exits through orifices 234. The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼" in width × 3" in length and employed in standard air freshening apparatus.

On operation of the standard air freshening apparatus as a room air freshener, after 4 minutes, the room has an aesthetically pleasing aroma as set forth, supra.

EXAMPLE III(E)

Deodorant Stick

A deodorant stick composition is prepared containing the following materials:

| Ingredients | Parts by Weight |
|---|---|
| Propylene Glycol | 65.00 |
| Sodium stearate | 7.00 |
| Distilled water | 23.75 |
| IRGSAN ® DP-300 (2,4,4-trichloro-2'-hydroxy diphenyl ether, manufactured by the Ciba Geigy Chemical Company and the trademark of the Ciba Geigy Chemical Company of Hastings on Hudson, New York) | 0.25 |
| Ground polymer containing one or a mixture of the mercaptans having the structures: 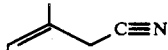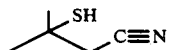 and  prepared according to Example III(D), supra. | 4.00 |

The ingredients are combined without the ground polymer and are heated to 75° C. These ingredients are mixed and continued to be heated until the sodium stearate has dissolved. The resulting mixture is cooled to 40° C. and the ground fragrance-containing polymer is added and mixed at 40° C. until a suspension is formed. The resulting suspension is cooled and formed into sticks and the deodorant sticks exhibit a pleasant fresh green aroma when utilized in the axillary areas of a human being.

EXAMPLE IV

Grapefruit Flavor Formulation

The following formulation is prepared:

| Ingredients | Parts by Weight EXAMPLE | | |
|---|---|---|---|
| | IV(A) | IV(B) | IV(C) |
| Grapefruit oil | 92.0 | 92.0 | 92.0 |
| Bergamot oil | 2.0 | 2.0 | 2.0 |
| Citral | 3.0 | 3.0 | 3.0 |
| n-Amyl alcohol | 1.0 | 1.0 | 1.0 |
| Ethyl acetate | 1.0 | 1.0 | 1.0 |
| 2-Methyl-4-phenyl-1-pentanol produced according to U.S. Pat. No. 4,632,831 | 1.5 | 0.0 | 0.0 |
| 2-Methyl-4-phenyl-1-pentanol acetate produced according to U.S. Pat. No. 4,632,831 | 0.0 | 1.8 | 0.0 |
| Tetrahydro-5-isopropyl-2-methyl-2-thiophene acetonitrile produced according to Example I, supra | 2.0 | 2.0 | 0.0 |
| One of the mercaptans having one of the structures: 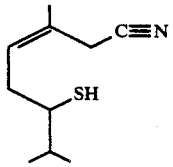 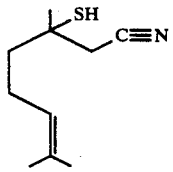 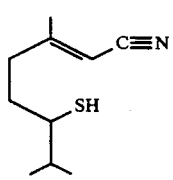 and 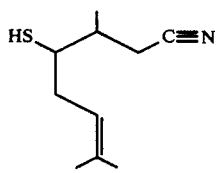 prepared according to Example I, supra. | 0.0 | 0.0 | 1.0 |

When the above grapefruit formulations are added to water at the rate of 1%, an excellent grapefruit drink is prepared. The tetrahydro-5-isopropyl-2-methyl-2-thiophene acetonitrile as well as each of the mercaptans having the structures:

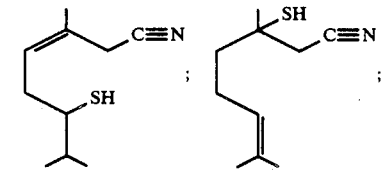

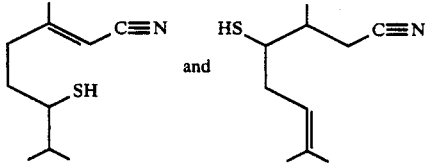

of our invention gives a minty, natural green nuance to the above two formulations thereby rendering them more "natural-like". Furthermore, the formulation are both "nootkatone" like with aesthetically pleasing red grapefruit notes.

When the above formulations are modified by adding to them 1.5 parts by weight of any of the following ingredients a yet more natural grapefruit peel aroma and taste is imparted thereto:
(1,3-diethylacetonyl)(1,3-diisopropylacetonyl)sulfide;
3-methyl-thio-4-heptanone;
3-propyl-thio-4-heptanone;
3-(methallylthio)-2,6-dimethyl-4-heptanone;
3-crotylthio-2,6-dimethyl-4-heptanone; and
3-allylthio-2,6-dimethyl-4-heptanone.

EXAMPLE v (I) The following concentrates are prepared:

| Ingredients | Parts by Weight | |
|---|---|---|
| | V(A) | V(B) |
| Geraniol | 1.00 | 1.00 |
| Ethyl methyl phenyl glycidate | 3.50 | 3.50 |
| Nootkatone | 5.00 | 5.00 |
| Ethyl pelargonate | 5.00 | 5.00 |
| Isoamyl acetate | 4.00 | 4.00 |
| Vanillin | 2.00 | 2.00 |
| Isobutyl-2-methyl-pentenoate | 3.00 | 3.00 |
| 2-Methyl-4-phenyl-1-pentanol | 1.00 | 1.00 |
| 2-Methyl-4-phenyl-1-pentanol acetate | 1.13 | 1.13 |
| Tetrahydro-5-isopropyl-2-methyl-2-thiophene acetonitrile | 1.00 | 0.00 |

One of the mercaptan having the structures:

| Ingredients | Parts by Weight | |
|---|---|---|
| | V(A) | V(B) |
| 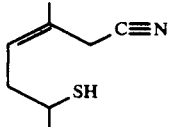 and 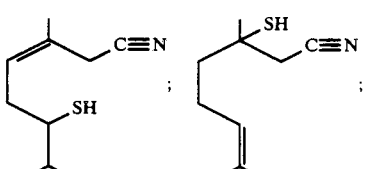 | 0.00 | 0.50 |

(II) One volume of one of the concentrates prepared in Part (I), supra, is dissolved in four volumes of propylene glycol and the mixture is added to a hard candy melt at the rate of 1.5 ounces of the concentrate solution per 100 pounds of melt. After the finished candy has been produced, it is found to have an excellent grapefruit flavor. When the candy is compared with candy made under the same conditions but without the tetrahydro-5-isopropyl-2-methyl-2-thiophene acetonitrile or one of the mercaptans having the structures:

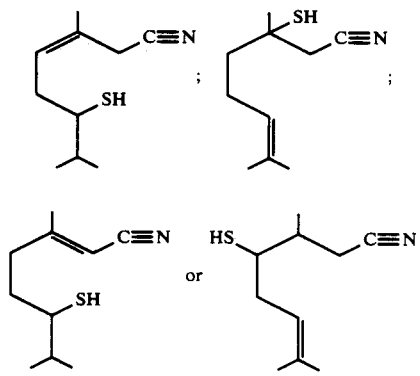

of out invention, it is found to have an inferior grapefruit flavor. Indeed, the grapefruit flavor used with the tetrahydro-5-isopropyl-2-methyl-2-thiophene acetonitrile or one of the mercaptans having the structures:

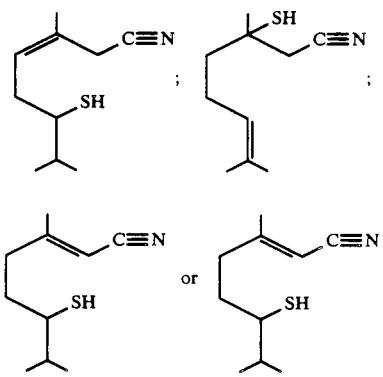

of our invention is markedly superior than without the tetrahydro-5-isopropyl-2-methyl-2-thiophene acetonitrile or mercaptans of our invention.

EXAMPLE VI

A. Powder Flavor Formulation

Twenty grams of one of the flavor formulations of Example IV is emulsified in a solution containing 300 grams gum acacia and 700 grams of water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| One of the Liquid grapefruit flavors of Example IV | 20 |
| Propylene glycol | 9 |
| CAB-O-SIL ® M-5 (Brand of silica produced by the Cabot Corporation of 125 High Street, Boston, Mass. 02110); | 5 |
| Physical Properties: | |
| Surface area: 200 m₂/gram Nominal particle size: 0.012 microns Density: 2.3 lbs./cu.ft. | |

The CAB-O-SIL ® is dispersed in one of the liquid grapefruit flavor compositions of Example IV with vigorous stirring thereby resulting in a viscous liquid. 71 Parts by weight of the powder flavor composition of Part "A", supra, is then blended into said viscous liquid with stirring at 25° C. for a period of thirty minutes resulting in a dry, free-flowing, sustained release grapefruit flavored powder.

EXAMPLE VII

Ten parts by weight of 50 Bloom pigskin gelatin is added to ninety parts by weight of water at a temperature of 150° C. The mixture is agitated until the gelatin is completely dissolved and the solution is cooled to 120° F. Twenty parts by weight of one of the liquid grapefruit flavor compositions of Example IV is added to the solution which is then homogenized to form an emulsion having a particle size typically in the range of 5-40 microns. The material is kept at 120° F. under which conditions the gelatin will not jell.

Coacervation is induced by adding slowly and uniformly forty parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting jelled coacervate may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE VIII

Chewing Gum

One hundred parts by weight of chicle are mixed with four parts by weight of one of the flavors prepared in accordance with Example VI(B). Three hundred parts of sucrose and one hundred parts of corn syrup are added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant long-lasting grapefruit flavor.

EXAMPLE IX

Chewing Gum

One hundred parts by weight of chicle are mixed with eighteen parts by weight of one of the flavors prepared in accordance with Example VII. Three hundred parts of sucrose and one hundred parts of corn syrup are then added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant, long-lasting grapefruit flavor.

EXAMPLE X

Toothpaste Formulation

The following separate groups of ingredients are prepared:

| Parts by Weight | Ingredient |
| --- | --- |
| Group "A" | |
| 30.200 | Glycerine |
| 15.325 | Distilled water |
| .100 | Sodium benzoate |
| .125 | Saccharin sodium |
| .400 | Stannous flurode |
| Group "B" | |
| 12.500 | Calcium carbonate |
| 37.200 | Dicalcium phosphate dihydrate |
| Group "C" | |
| 2.000 | Sodium n-lauroyl sarcosinate (foaming agent) |
| Group "D" | |
| 1.200 | One of the flavor materials of Example VI(B). |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized and finally tubed.

The resulting toothpaste, when used in a normal toothbrushing procedure, yields a pleasant grapefruit flavor of constant strong intensity throughout said procedure (1-1.5 minutes).

EXAMPLE X

Chewable Vitamin Tablets

One of the flavor materials produced according to the process of Example VII is added to a chewable vitamin tablet formulation at the rate of ten grams per kilogram which chewable vitamin tablet formulation is prepared as follows:

In a Hobart mixer, the following materials are blended to homogeneity:

| Ingredients | Grams/1000 Tablets |
| --- | --- |
| Vitamin C (ascorbic acid as ascrobic acid-sodium ascorbate mixture 1:1 | 70.110 |
| Vitamin $B_1$ (thiamine mononitrate as ROCOAT ® thiamine mononitrate 33⅓% (Hoffman LaRoche) | 4.000 |
| Vitamin $B_2$ (riboflavin) as ROCOAT ® riboflavin 33⅓% | 5.000 |
| Vitamin $B_6$ (pyridoxine hydrochloride) as ROCOAT ® phridoxine hydrochloride 33⅓% | 4.000 |
| Niacinamide as ROCOAT ® niacinamide 33⅓% | 33.000 |
| Calcium pantothenate | 11.500 |
| Vitamin $B_{12}$ (cyanocobalamin) as Merck 0.1% in gelatin | 3.500 |
| Vitamin E (dl-alpha tocopheryl cetate) as dry Vitamin E acetate 33⅓% | 6.600 |
| d-Biotin | 0.044 |
| One of the flavor materials of Example VII | (as indicated above) |
| Certified lake color | 5.000 |
| Sweetener, sodium saccharin | 1.000 |
| Magnesium stearate lubricant | 10.000 |
| Mannitol q.s. to make | 500.000 |

Preliminary tablets are prepared by slugging with flat-faced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong grapefruit flavor for a period of 12 minutes.

EXAMPLE XII

Herbal Perfume Formulation

The following mixtures are prepared:

| Ingredients | Parts by Weight EXAMPLES | | |
|---|---|---|---|
| | XI(A) | XI(B) | XI(C) |
| Oakmoss absolute (50% in diethyl phthalate) | 20 | 20 | 20 |
| Alpha-methyl-3,4-methylene-dioxyhydrocinnamic aldehyde | 10 | 10 | 10 |
| Methyl dihydrojasmonate | 100 | 100 | 100 |
| Coumarin | 20 | 20 | 20 |
| Musk ketone | 80 | 80 | 80 |
| Isocyclocitral (10% in diethyl phthalate) | 10 | 10 | 10 |
| Galbanum oil (10% in diethyl phthalate) | 6 | 6 | 6 |
| Rosemary oil | 10 | 10 | 10 |
| Pine needle oil | 60 | 60 | 60 |
| Fir balsam absolute (10% in diethyl phthalate) | 10 | 10 | 10 |
| Bergamot oil | 60 | 60 | 60 |
| Lemon oil | 14 | 14 | 14 |
| Benzyl acetate | 468 | 468 | 468 |
| Linalool | 80 | 80 | 80 |
| Indole (10% in diethyl phthalate) | 6 | 6 | 6 |
| Undecalactone (10% in diethyl phthalate) | 12 | 12 | 12 |
| 2-methyl-4-phenyl-1-pentanol (produced according to U.S. Pat. No. 4,632,831) | 12 | 0 | 0 |
| 2-methyl-4-phenyl-1-pentanol acetate (produced according to U.S. Pat. No. 4,632,831) | 0 | 20 | 5 |
| Tetrahydro-5-isopropyl-2-methyl-2-thiophene acetonitrile produced according to Example I, supra. | 10 | 5 | 0 |
| One of the mercaptans having the structures: | 0 | 0 | 5 |

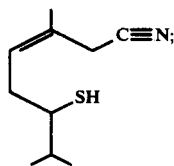
;

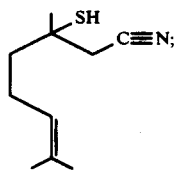
;

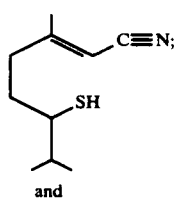
;

and

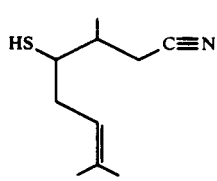

| Ingredients | Parts by Weight EXAMPLES | | |
|---|---|---|---|
| | XI(A) | XI(B) | XI(C) |
| prepared according to Example I, supra. | | | |

The addition to this herbal formulation of the tetrahydro-5-isopropyl-2-methyl-2-thiophene acetonitrile or one of the mercaptans having one of the structures:

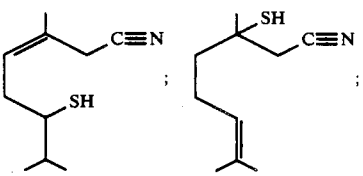

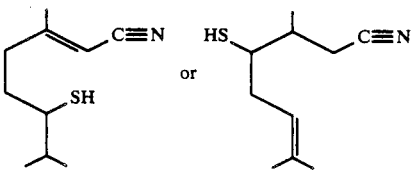

imparts to this herbal formulation an excellent natural buchu leaf, tomato leaf, herbaceous, basil, minty and grapefruit-like topnotes, with natural "ontiga", tomato leaf, minty and grapefruit-like undertones. Accordingly, the formulations can be described as "herbaceous with natural buchu leaf, tomato leaf, herbaceous, basil, minty and grapefruit-like topnotes and natural "ontiga", tomato leaf, minty and grapefruit-like undertones".

EXAMPLE XIII

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| Tetrahydro-5-isopropyl-2-methyl-2-thiophene acetonitrile produced according to Example I. | A natural buchu leaf, tomato leaf, herbaceous, basil, minty and grapefruit-like aroma profile with natural "ontiga", tomato leaf, minty and grapefruit-like undertones. |
| The mercaptan having the structure: | A natural buchu leaf, tomato leaf, herbaceous, basil, minty and grapefruit-like aroma profile with natural "ontiga", tomato leaf, minty and grapefruit-like undertones, having an intensity twofold that of the compound having the structure: |

TABLE II-continued

| Substance | Aroma Description |
|---|---|
| 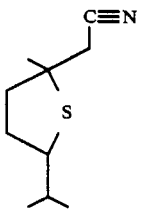<br>produced according to Example I. | |
| The compound having the structure:<br>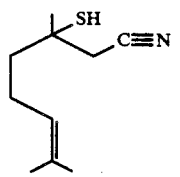<br>produced according to Example I. | A natural buchu leaf, tomato leaf, herbaceous, basil, minty and grapefruit-like aroma profile with natural "ontiga", tomato leaf, minty and grapefruit-like undertones, |
| The compound having the structure:<br>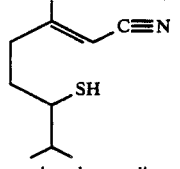<br>produced according to Example I. | A natural buchu leaf, tomato leaf, herbaceous, basil, minty and grapefruit-like aroma profile with natural "ontiga", tomato leaf, minty and grapefruit-like undertones, |
| The compound having the structure:<br>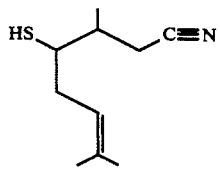<br>produced according to Example I. | A natural buchu leaf, tomato leaf, herbaceous, basil, minty and grapefruit-like aroma profile with natural "ontiga", tomato leaf, minty and grapefruit-like undertones, |
| Perfume formulations of Example XII. | A herbaceous aroma with natural buchu leaf, tomato leaf, herbaceous, basil, minty and grapefruit-lile topnotes and natural "ontiga", tomato leaf, minty and grapefruit-like undertones. |

EXAMPLE XVI

Perfumed Liquid Detergents

Concentrated liquid detergents (Lysine salt of n-dodecylbenzene sulfonic acid as more specifically described in U.S. Pat. No. 3,948,818 issued Apr. 6, 1976 incorporated by reference herein) with aroma nuances as set forth in Table II of Example XIII are prepared containing 0.10%, 0.15%, 0.20%, 0.25%, 0.30% and 0.35% of the substance set forth in Table II of Example SII. They are prepared by adding and homogeneously mixing the appropriate quantity of substance set forth in Table II of Example XIII in the liquid detergent. The detergents all possess excellent aromas as set forth in Table II of Example XIII, the intensity increasing with greater concentrations of substance as set forth in Table II of Example XIII.

EXAMPLE XV

Preparation of Colognes and Handkerchief Perfumes

Compositions as set forth in Table II of Example XIII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table II of Example XIII are imparted to the colognes and to the handkerchief perfumes at all levels indicated.

EXAMPLE XVI

Preparation of Soap Compositions

One hundred grams of soap chips (per sample)-(IVORY ®, produced by the Procter & Gamble Company of Cincinnati, Ohio), are each mixed with one gram samples of substances as set forth in Table II of Example XIII until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table II of Example XIII.

EXAMPLE XVII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "NEODOL ® 45-11 (a $C_{14}$—$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example XIII. Each of the detergent samples has an excellent aroma as indicated in Table II of Example XIII.

EXAMPLE XVIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper"); and
2. Adogen 448 (m.p. about 140° F.) as the substrate coating; and pH3. An outer coating having the following formulation (m.p. about 150° F.):
57%—$C_{20-22}$ HAPS
22%—isopropyl alcohol 20%—antistatic agent 1%—of one of the substances as set forth in Table II of Example XIII.

Fabric softening compositions prepared according to Example I at column 15 of U.S. Pat. No. 3,632,396 having aroma characteristics as set forth in Table II of Example XIII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XIII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example XIII, supra.

EXAMPLE XIX

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

|  | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example XIII, supra | 0.10 |

The perfuming substances as set forth in Table II of Example XIII add aroma characteristics as set forth in Table II of Example XIII which are rather intense and aesthetically pleasing to the users of the soft-feel, good-hold pump hair sprays.

EXAMPLE XX

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol disterate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C). This material is "COMPOSITION A".

GAFQUAT ® 755N polymer (manufactured by GAF Corporation of 140 West 51st Street, New York, N.Y.)(5.0 weight percent) is admixed with 0.1 weight percent sodium sulfite and 1.4 percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example XIII is added to the mixture. The resulting mixture is cooled to 40° C. and blending is carried out for an additional one hour in each case. At the end of this blending period, the resulting material has a pleasant fragrance as indicated in Table II of Example XIII.

EXAMPLE XXI(A)

Impregnated Plastics and Air Fresheners

Scented polyethylene pellets having a pronounced green, floral and rose aroma are prepared as follows:

75 Pounds of polyethylene having a melting point of about 220° F. is heated to about 230° F. in a container of the kind illustrated in FIGS. 11 and 12. 12.5 Pounds of S(4-hydroxy-1-isopropyl-4-methylhexyl) thioacetate prepared according to Example II are then quickly added to the liquified polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the S(4-hydroxy-1-isopropyl-4-methylhexyl) thioacetate-containing material through the orifices 234 whereby such material exits through orifices 234. The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼" in width × 3" in length and employed in standard air freshening apparatus.

On operation of the standard air freshening apparatus as a room air freshener, after 4 minutes, the room has an aesthetically pleasing aroma as set forth, supra.

EXAMPLE XXI(B)

Treated Plastics and Air Freshener

100 Pounds of polypropylene are heated to about 300° F. 15 Pounds of S(4-hydroxy-1-isopropyl-4-methylhexyl) thioacetate prepared according to Example II are added to the liquified polypropylene. The procedure is carried out in the apparatus shown in FIGS. 11 and 12. After mixing for about 8 minutes, the valve "V" is opened to allow the exit of polypropylene mixture which has been treated with the S(4-hydroxy-1-isopropyl-4-methylhexyl) thioacetate, whereby solid pellets having pronounced aromas described as green, floral and rose are formed on the conveyor. The pellets thus obtained are then admixed with about 20 times their weight of unscented polypropylene ad untreated polypropylene and the mixture is heated and molded into "spaghetti" tows. The "spaghetti" tows are cut into small cylinders approximately 0.1 inches in length × 0.2 inches in diameter. The cylinders have strong and pleasant aromas as described, supra.

The cylinders are used in standard air freshening apparatus to produce aesthetically pleasing aromas as set forth, supra with no foul odors in envirnonments surrounding the air freshener apparatus.

A portion of the cylinders are ground into small particles to be used in the deodorant stick of Example XXI(C), infra.

EXAMPLE XXI(C)

Deodorant Stick

A deodorant stick composition is prepared containing the following materials:

| Ingredients | Parts by Weight |
| --- | --- |
| Propylene Glycol | 65.00 |
| Sodium stearate | 7.00 |
| Distilled water | 23.75 |
| IRGSAN ® DP-300 (2,4,4-trichloro-2'-hydroxy diphenyl ether, manufactured by the Ciba Geigy Chemical Company of Hastings On Hudson, New York) | 0.25 |
| Ground polymer containing fragrance produced according to Example XXI(B), supra. | 4.00 |

The ingredients are combined without the ground polymer and heated to 75° C. These ingredients are mixed and continued to be heated until the sodium stearate has dissolved. The resulting mixture is cooled to 40° C. and the ground fragrance-containing polymer is added and mixed at 40° C. until the suspension is formed. The resulting suspension is cooled and formed into sticks and the deodorant sticks exhibit a pleasant, fresh, green, floral, rose aroma when utilized in the axillary areas of a human being.

EXAMPLE XXII

Herbal Perfune Formulation

The following mixtures are prepared:

| Ingredients | Parts by Weight EXAMPLES | | |
| --- | --- | --- | --- |
| | XXII(A) | XXII(B) | XXII(C) |
| Oakmoss absolute (50% in diethyl phthalate) | 20 | 20 | 20 |
| Alpha-methyl-3,4-methylene-dioxyhydrocinnamic aldehyde | 10 | 10 | 10 |
| Methyl dihydrojasmonate | 100 | 100 | 100 |
| Coumarin | 20 | 20 | 20 |
| Musk ketone | 80 | 80 | 80 |
| Isocyclocitral (10% in diethyl phthalate) | 10 | 10 | 10 |
| Galbanum oil (10% in diethyl phthalate) | 6 | 6 | 6 |
| Rosemary oil | 10 | 10 | 10 |
| Pine needle oil | 60 | 60 | 60 |
| Fir balsam absolute (10% in diethyl phthalate) | 10 | 10 | 10 |
| Bergamot oil | 60 | 60 | 60 |
| Lemon oil | 14 | 14 | 14 |
| Benzyl acetate | 468 | 468 | 468 |
| Linalool | 80 | 80 | 80 |
| Indole (10% in diethyl phthalate). | 6 | 6 | 6 |
| Undecalactone (10% in diethyl phthalate). | 12 | 12 | 12 |
| 2-Methyl-4-phenyl-1-pentanol prepared according to U.S. Pat. No. 4,632,831. | 12 | 0 | 0 |
| 2-Methyl-4-phenyl-1-pentanol acetate prepared according to U.S. Pat. No. 4,632,831. | 0 | 20 | 0 |
| S(4-hydroxy-1-isopropyl-4-methylhexyl)thioacetate prepared according to Example II, supra. | 10 | 20 | 15 |
| Mixture of S(4-hydroxy-1-isopropyl-4-methylhexyl) thioacetate having the structure: | 0 | 0 | 5 |

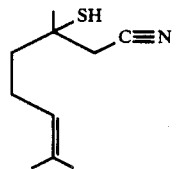

and

The compound having the structure:

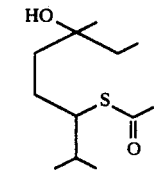

The addition to this herbal formulation of the S(4-hydroxy-1-isopropyl-4-methylhexyl) thioacetate imparts to this herbal formulation excellent green, floral and rose undertones. Accordingly, the formulations of Examples XXII(A) and XXII(B) can be described as "herbaceous, with green, floral and rose undertones".

The addition of the mixture of the compound having the structure:

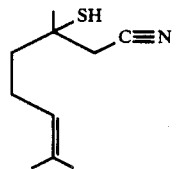

and the compound having the structure:

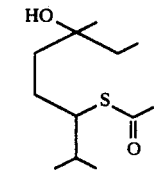

to this herbal formulation imparts to the herbal formulation excellent green, floral, rose, natural "buchu" leaf, tomato leaf, basil minty and grapefruit-like topnotes and natural "ontiga", tomato leaf, minty and grapefruit-like undertones. Accordingly, the formulation of Example XXII(C) can be described as "herbaceous" with green, floral, rose, natural "buchu" leaf, tomato leaf, basil, minty and grapefruit-like topnotes and natural "ontiga", tomato leaf, minty and grapefruit-like" undertones.

EXAMPLE XXIII

Preparation of Cosmetic Powder Compositions

Cosmetic powder compositions are prepared by mixing in a ball mill 100 grams of talcum powder with 0.25 grams of each of the substances set forth in Table III below. Each of the cosmetic powder compositions has an excellent aroma as described in Table III below.

TABLE III

| Substance | Aroma Description |
|---|---|
| S(4-hydroxy-1-isopropyl-4-methylhexyl thioacetate having the structure: 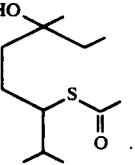 | A green, floral, rose aroma profile. |
| Perfume composition of Example XXII(A). | A herbaceous aroma with green, floral and rose undertones. |
| Perfume composition of Example XXII(B). | A herbaceous aroma with green, floral and rose undertones. |
| Perfume composition of Example XXII(C). | Herbaceous with green, floral, rose, natural "buchu" leaf, tomato leaf, basil, minty and grapefruit-like topnotes and natural "ontiga", tomato leaf, minty and grapefruit-like undertones. |

EXAMPLE XXIV

Perfumed Liquid Detergents

Concentrated liquid detergents (Lysine salt of n-dodecylbenzene sulfonic acid as more specifically described in U.S. Pat. No. 3,948,818 issued Apr. 6, 1976 incorporated by reference herein) with aroma nuances as set forth in Table III of Example XXIII are prepared containing 0.10%, 0.15%, 0.20%, 0.25%, 0.30% and 0.35% of the substance set forth in Table III of Example XXIII. They are prepared by adding and homogeneously mixing the appropriate quantity of substance set forth in Table III of Example XXIII in the liquid detergent. The detergents all possess excellent aromas as set forth in Table III of Example XXIII, the intensity increasing with greater concentrations of substance as set forth in Table III of Example XXIII.

EXAMPLE XXV

Preparation of Colognes and handkerchief Perfumes

Compositions as set forth in Table III of Example XXIII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table III of Example XXIII are imparted to the colognes and to the handkerchief perfumes at all levels indicated.

EXAMPLE XXVI

Preparation of Soap Compositions

One hundred grams of soap chips (per sample)-(IVORY®, produced by the Procter & Gamble Company of Cincinnati, Ohio), are each mixed with one gram samples of substances as set forth in Table III of Example XXIII until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table III of Example XXIII.

EXAMPLE XXVII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "NEODOL ® 45-11 (a $C_{14}$—$C_{15}$ alcohol ethoxylanted with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table III of Example XXIII. Each of the detergent samples has an excellent aroma as indicated in Table III of Example XXIII.

EXAMPLE XXVIII

Utilizing the procedure of Example I at column 15 of U.S. Pat. No. 3,632,396 (the disclosure of which is incorporated herein by reference), nonwoven cloth substrates useful as drier-added fabic softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and a pH of 3. An outer coating having the following formulation (m.p. about 150° F.):
   57%—$C_{20-22}$ HAPS
   22%—isopropyl alcohol
   20%—antistatic agent
   1%—of one of the substances as set forth in Table III of Example XXIII.

Fabric softening compositions prepared according to Example I at column 15 of U.S. Pat. No. 3,632,396 having aroma characteristics as set forth in Table III of Example XXIII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table III of Example XXIII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table III of Example XXIII, supra.

EXAMPLE XXIX

Hair Spray Formulations

The following hair spray formulation is prepared by first dissolving PVP/VA E-735 copolymer manufactured by the GAF Corporation of 140West 51st Street, New York, N.Y. in 91.62 grams of 95% food grade ethanol 8.0 Grams of the polymer is dissolved in the alcohol. The following ingredients are added to the PVP/VA alcoholic solution:

|  | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table III of Example XXIII, supra. | 0.10 |

The perfuming substances as set forth in Table III of Example XXIII add aroma characteristics as set forth in Table III of Example XXIII which are rather intense and aesthetically pleasing to the users of the soft-feel, good hold pump hair sprays.

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table III of Example XXIII.

What is claimed is:

1. A cyayno-substituted sulfur-containing compound defined according to a structure selected from the group consisting of:

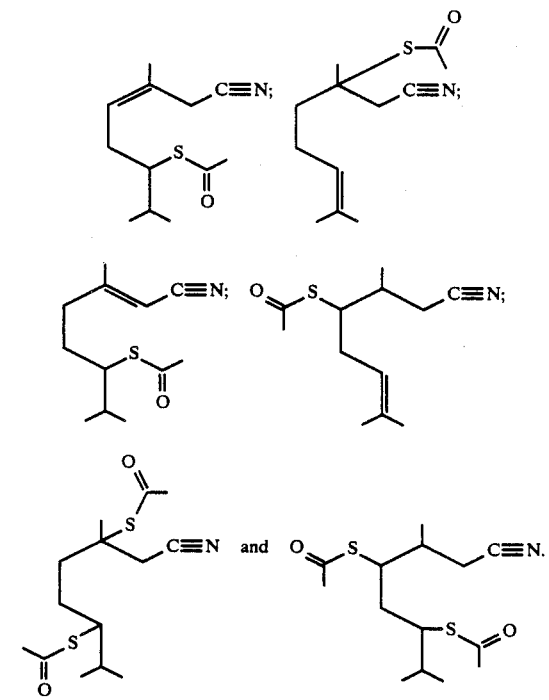

2. A product produced according to the process of reacting geranonitrile with thioacetic acid thereby yielding a mixture of cyano-substituted sulfur-containing compounds.

3. A process for augmenting or enhancing the aroma or taste of a consumable material comprising the step of adding to said consumable material, an aroma or taste augmenting or enhancing quantity of the product defined according to claim 1.

4. A process for augmenting or enhancing the aroma or taste of a consumable material comprising the step of adding to said consumable material, an aroma or taste augmenting or enhancing quantity of the product defined according to claim 2.

* * * * *